(12) United States Patent
Korampally et al.

(10) Patent No.: US 9,181,571 B2
(45) Date of Patent: Nov. 10, 2015

(54) REUSABLE PCR AMPLIFICATION SYSTEM AND METHOD

(71) Applicant: THE CURATORS OF THE UNIVERSITY OF MISSOURI, Columbia, MO (US)

(72) Inventors: Venumadhav Korampally, Columbia, MO (US); Shubhra Gangopadhyay, Columbia, MO (US); Keshab Gangopadhyay, Columbia, MO (US); Sheila A. Grant, Columbia, MO (US); Steven B. Kleiboeker, Lee's Summit, MO (US); Shantanu Bhattacharya, West Lafayette, IN (US); Yuanfang Gao, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 14/488,734

(22) Filed: Sep. 17, 2014

(65) Prior Publication Data

US 2015/0004648 A1   Jan. 1, 2015

Related U.S. Application Data

(62) Division of application No. 14/021,599, filed on Sep. 9, 2013, now abandoned, which is a division of application No. 13/416,288, filed on Mar. 9, 2012, now Pat. No. 8,545,769, which is a division of application No. 12/097,516, filed as application No. PCT/US2006/047722 on Dec. 15, 2006, now Pat. No. 8,173,077.

(60) Provisional application No. 60/750,790, filed on Dec. 16, 2005.

(51) Int. Cl.
*C12P 19/34* (2006.01)
*C12Q 1/68* (2006.01)
*B01L 3/00* (2006.01)
*B01L 7/00* (2006.01)

(52) U.S. Cl.
CPC ............... *C12P 19/34* (2013.01); *B01L 3/5027* (2013.01); *B01L 3/502707* (2013.01); *C12Q 1/686* (2013.01); *C12Q 1/6844* (2013.01); *B01L 7/52* (2013.01); *B01L 2200/12* (2013.01); *B01L 2300/0816* (2013.01); *B01L 2300/0867* (2013.01); *B01L 2300/123* (2013.01); *B01L 2300/1827* (2013.01); *B01L 2400/0421* (2013.01); *B01L 2400/0481* (2013.01)

(58) Field of Classification Search
CPC ........... C12Q 1/6869; C12Q 2565/629; C12Q 1/6844; B01L 3/5027; C08L 83/04; C12M 23/16; G01N 27/44791; B81B 1/00; B81C 1/00; C08G 77/38
USPC ......................... 422/500; 435/6.1, 91.2, 287.2
See application file for complete search history.

(56) References Cited

U.S. PATENT DOCUMENTS

2004/0209354 A1 * 10/2004 Mathies et al. ............ 435/287.2

OTHER PUBLICATIONS

Kohl, Abbe T. et al. "Low k, Porours Methyl Silsesquioxane and Spin-On-Glass," Electrochemical and Solid-State Letters, 2(2), 1999, p. 77-79.*

*Primary Examiner* — Dennis M White
*Assistant Examiner* — Bryan Kilpatrick
(74) *Attorney, Agent, or Firm* — Shook, Hardy & Bacon L.L.P.

(57) ABSTRACT

A DNA amplification device utilizing a polydimethylsiloxane (PDMS) and silicon substrate coated with spin-on glass (SOG) is provided. This PDMS layer is irreversibly bonded to the SOG layer of the silicon substrate using oxygen plasma. The amplification device is an inexpensive, microfluidic device, which can be utilized as a portable thermo-cycler to perform PCR amplification of DNA in the field.

5 Claims, 31 Drawing Sheets

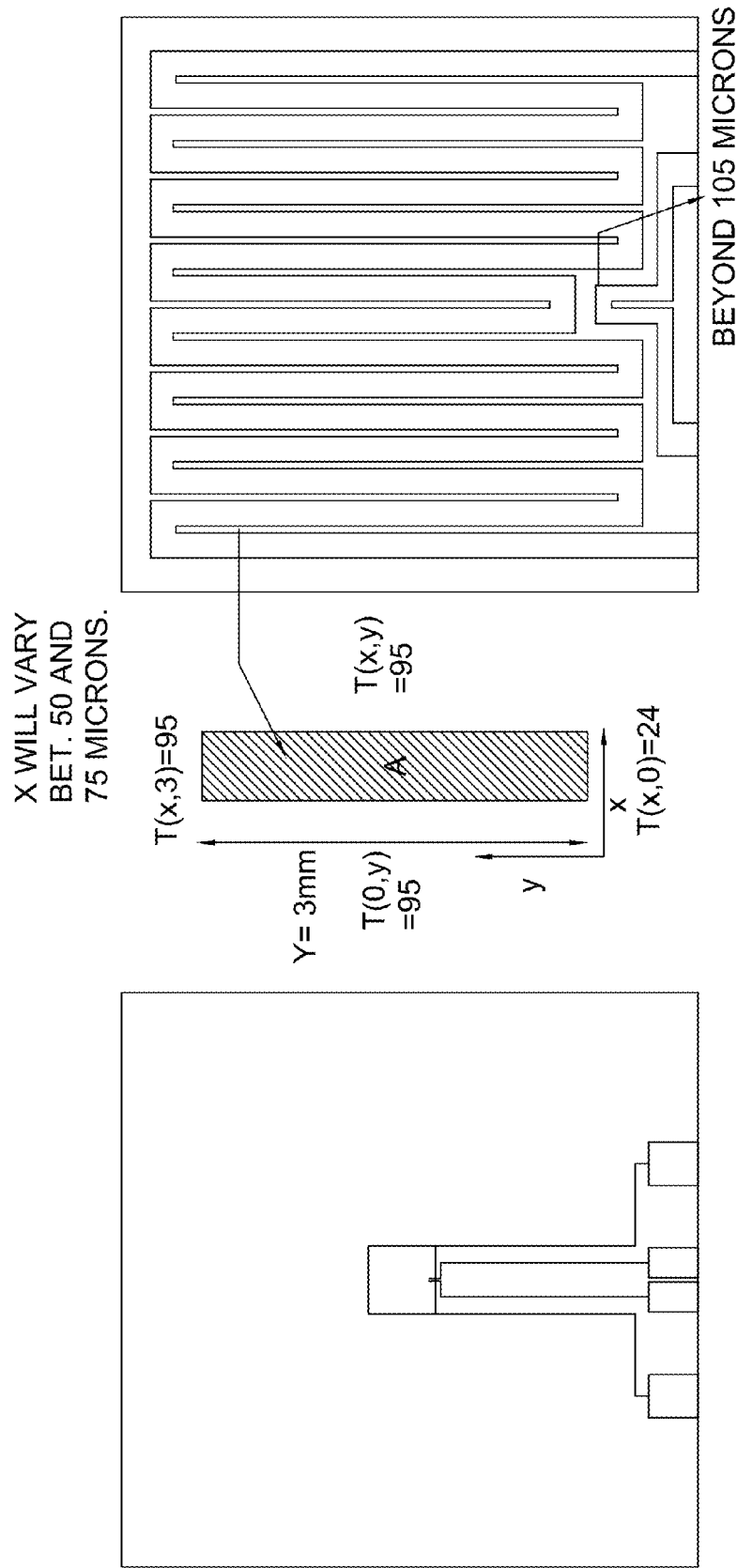
FIG. 2 (A) PLANTINUM HEATERS AND RTD ASSEMBLY MASK. (B) MAGNIFIED VIEW OF THE HEATERS WITH DESCRIPTION OF THE BOUNDARY CONDITION AND X-Y SCALE.

MASK DESIGN FOR A HEATER AND RTD INTEGRATED ON A SINGLE CHIP

TEMPERATURE DISTRIBUTION PLOT FOR THE HEATER DESIGN IN 4A

PLOT OF BAND STRENGTH AND CONTACT ANGLE WITH VARIATION IN CHAMBER PRESSURE

PLOT OF BOND STRENGTH AND CONTACT ANGLE WITH TIME OF EXPOSURE

SEQUENCE OF BLISTER INFLATION

| TEMPERATURE (DEG. C) | HOLD TIME (SECS) | NO. OF CYCLES |
|---|---|---|
| 95 | 12 MINS. | 1 CYCLE |
| 95 | 30 SECS. | 15 CYCLES |
| 72 | 30 SECS. | |
| 72 | 1 MIN AND 30 SECS. | |
| 95 | 30 SECS. | |
| 71 | 30 SECS. | |
| 72 | 1 MIN AND 30 SECS. | |
| -- | SAME | |
| -- | SAME | |
| 95 | 30 SECS. | 35 CYCLES |
| 58 | 30 SECS. | |
| 72 | 1 MIN. | |
| -- | SAME | |
| -- | SAME | |

FIG. 11

SLAB GEL IMAGE FOR PRODUCTS
OF THE ON CHIP AMPLIFIER.

GAUSSIAN FIT ATR-FTIR SPECTRA OF METHYL GROUP
FOR UNTREATED SOG AFTER PLASMA TREATMENT

GAUSSIAN FIT ATR-FTIR SPECTRA OF OH ABSORPTION
BAND FOR UNTREATED SOG AFTER PLASMA TREATMENT

| | |
|---|---|
| Before exposure | Immediately after exposure |
| Contact angle = 83.01 | Contact angle = 7.049 |
| After 5 mins | After 1 hours |
| Contact angle = 12.75 | Contact angle = 31.68 |
| After 5 hours | After 2 days |
| Contact angle = 62.41 | Contact angle = 63.94 |

FIG. 15.

REUSABLE PCR AMPLIFICATION SYSTEM AND METHOD

CROSS REFERENCE TO RELATED APPLICATIONS

This application, is a Divisional Application of copending U.S. application Ser. No. 14/021,599, filed Sep. 9, 2013, entitled "Reusable PCR Amplification System and Method;" which is a Divisional Application of U.S. Pat. No. 8,545,769, filed Mar. 9, 2012, issued on Oct. 1, 2013, and entitled "Reusable PCR Amplification System and Method;" which is a Divisional Application of U.S. Pat. No. 8,173,077 filed Jan. 28, 2009, issued on May 8, 2012, and entitled "Reusable PCR Amplification System and Method;" which was the National Stage of International Application No. PCT/US2006/047722, filed Dec. 15, 2006; which claims the benefit of priority to U.S. Provisional No. 60/750,790, filed on Dec. 16, 2005. Each of these applications is incorporated herein by reference in its entirety.

STATEMENT REGARDING FEDERALLY SPONSORED RESEARCH OR DEVELOPMENT

Not Applicable.

BACKGROUND

Several conventional methods are now available for performing PCR (polymerase chain reaction) amplification of a DNA sample using a device formed on a single chip. Unfortunately, these conventional methods suffer from several limitations that limit their commercial value. For example, some single chip devices cannot be used more than once due to residual DNA left behind in the device after amplification. Conventional devices also typically require long time periods for heating and cooling the device to required temperatures during an amplification process. Additionally, a minimum sample size and concentration of DNA to be amplified is usually required.

What is needed are a system and method for improved single chip amplification of DNA samples. The system and method should allow for faster amplification processes while using reduced volumes and concentrations of DNA samples. The system and method should also allow the same single chip platform to be used for multiple amplification processes.

SUMMARY

In an embodiment, the invention provides a system and method for performing PCR amplification of dilute and/or reduced volume samples of DNA. In an embodiment, the system and method allow for amplification of a DNA sample containing 1 picogram or less of DNA. In another embodiment, the system and method allow for amplification of a DNA sample having a sample size of 5 microliters or less.

In still another embodiment, the invention provides a single chip system and method for performing multiple DNA amplification procedures with a reusable chip. After performing a first DNA amplification procedure, a method is provided for cleaning the system. The cleaned system can then be used for a second DNA amplification procedure with minimal or no contamination due to the first procedure.

In yet another embodiment, the invention provides a method for constructing a reusable single chip system for DNA amplification. A spin-on glass (SOG, composed of methyl silsesquioxane) layer is deposited on a substrate. A polydimethylsiloxane (PDMS) layer is formed that defines at least one fluid path for performing amplification. The PDMS layer and the SOG layer are plasma treated in oxygen plasma to reduce the contact angle of the layers by making these surfaces hydrophilic. The contact angle of both of the surfaces is found to increase with post exposure relaxation time. After reducing the contact angle of the layers, the PDMS and SOG layers are bonded together. This produces a DNA amplification system having high contact angle (hydrophobic) interior walls while providing strong bond strength between the SOG and PDMS layers.

BRIEF DESCRIPTION OF THE DRAWINGS

FIGS. 2A-2B schematically depict a portion of a device according to an embodiment of the invention;

FIG. 11 depicts data for a method corresponding to an embodiment of the invention;

FIG. 15 depicts contact angles of post exposed SOG surface with relaxation time according to an embodiment of the present invention;

DETAILED DESCRIPTION

In various embodiments, a novel on-chip platform has been fabricated by optimizing the design and micro-fabrication processes using PDMS (Poly Dimethyl Siloxane) and Silicon. The silicon base contains a set of micro-fabricated platinum heater structures on the bottom with a 406 nm thick SOG (Spin On Glass) layer on the top. This structure is then irreversibly bonded using oxygen plasma to a 3 µl replica molded PDMS chamber with feed channels and inlet-outlet ports. The plasma exposed SOG surface is found to undergo recovery of hydro-phobicity with time as indicated by an increase in advancing contact angle by sessile drop method and attenuated total internal reflection-fourier transform infrared spectroscopy (ATR-FTIR). The protocol developed can be used for bonding PDMS to a diverse range of substrates, which may form a basis for integration of fluidic assays with microelectronics. A thermal cycler with flexible PCR cycle control is designed and implemented using labview software. Temperature control is achieved by a PID (proportional, integral, differential) controller using a thermocouple temperature sensor. Preferably, pulse width modulation technology can be used for this control. The temperature ramp up and down times have been reduced to almost ⅟₁₀th of the conventional thermo-cycler. A comparison made between contemporary continuous film based on chip heater designs and serpentine design shows a reduction of ramp up and down time by almost five times. Amplification has been tested using this platform for a 527-bp DNA of the Infectious Bovine Rhinetracheitis virus (IBR). An ethydium bromide stained agarose gel is used to detect the amplified product. The chip is an inexpensive, microfluidic cassette, which can be utilized as a portable thermo-cycler to perform PCR amplification of DNA in the field. In an embodiment, this device could be integrated with capillary electrophoresis and optical waveguide components to make a complete and compact DNA assay.

I. Structure of the Device

Figure 1A:
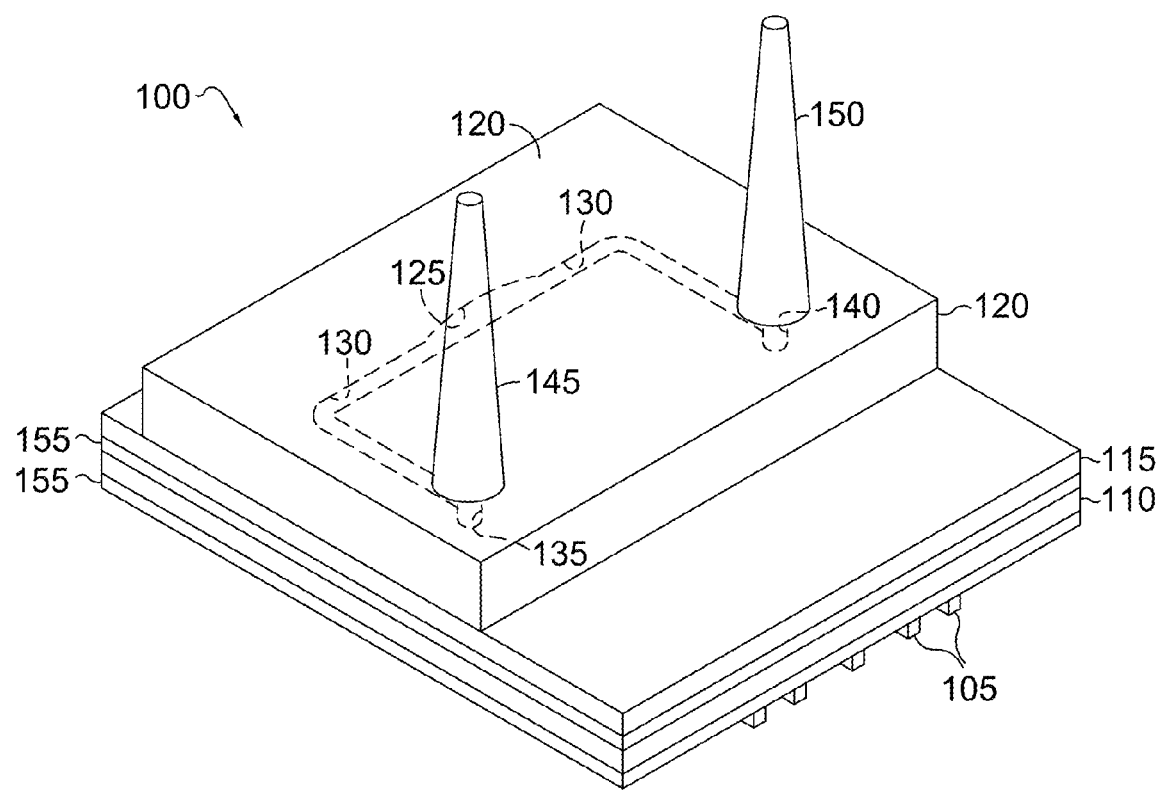
FIG. 1A schematically depicts a device according to an embodiment of the invention.

With reference to FIG. 1A, a polydimethylsiloxane (PDMS) device 100 is shown. Heater structures 105 are positioned on the bottom of a silicon substrate 110. The top surface of the silicon substrate 110 is spin-coated with a layer of Spin on Glass (SOG, methyl silsesquioxane) 115. A replica molded piece of PDMS 120 is bonded to the SOG layer 115 of the silicon substrate 110. A chamber 125 and channels 130 leading to inlet reservoirs 135 and outlet reservoirs 140 exist in between the SOG layer 115 and the molded PDMS 120. The inlet port 145 and outlet port 150 are mounted over the inlet reservoir 135 and outlet reservoir 140 respectively. A thermocouple may be incorporated into device 100 for monitoring the temperature.

A. Substrate Material

In an embodiment, the PCR amplification chamber is constructed on a silicon substrate 110. The silicon substrate can be formed from a conventional silicon wafer. The silicon substrate 110 can be referred to as having a top surface, where the PCR chamber 125 will be formed, and a bottom surface, where the heaters 105 are formed.

Preferably, an oxide layer 155 or another insulating layer is formed around the silicon substrate 110, or at least a portion of the silicon substrate 110. More preferably, the oxide formed includes an oxide layer 155 formed on the bottom surface of the silicon substrate 110. The oxide layer 155 should be thick enough to allow some electrical isolation of the heaters 105, but thin enough to allow efficient transfer of heat to the top surface of the silicon substrate 110. The insulating layer 155 can be formed by any convenient method, such as formation of an oxide layer by passing steam over a silicon surface heated to 1100° C. (wet thermal oxidation). In an embodiment, an oxide layer can be at least 500 nm, or at least 700 nm, or at least 800 nm, or at least 900 nm. In another embodiment, the oxide layer can be 1500 nm or less, or 1200 nm or less, or 1000 nm or less, or 900 nm or less.

B. SOG and PDMS Layers

In the embodiment depicted in FIG. 1A, SOG layer 115 represents an SOG layer formed by depositing a Filmtronics SOG precursor onto a wafer and spinning the wafer at roughly 8000 rpm. The SOG layer 115 is then subjected to a heating cycle to harden the layer, resulting in a layer with a thickness of roughly 400 nm. PDMS layer 120 is formed according to one of the procedures described below. After separating the PDMS slab from the negative photoresist mold, the PDMS slab can be exposed together with the SOG coated silicon wafer to an oxygen plasma in a plasma etcher. In FIG. 1A, the PDMS slayer 120 and SOG coated 115 silicon wafer 110 are exposed to a plasma formed using 20 W RIE power, 900 mTorr chamber pressure, 182 sccm oxygen flow rate and 35 secs time of exposure.

C. Heater Design and Formation

In various embodiments, one or more heaters 105 of FIG. 1A are formed on the bottom side of the silicon substrate 110. If an oxide layer 155 or other insulating layer is present, the heaters 105 are formed on the insulating layer 155. Due to the requirements for PCR processing, the heaters 105 are formed in order to maintain a temperature differential of ±1° C. or less throughout the amplification device. The design of the heaters 105 involves a tradeoff between several competing design goals. The heaters 105 occupy enough of the area below the amplification chamber 125 to maintain the desired temperature tolerances. The heaters 105 should also have a low enough resistance to maintain the desired temperature tolerances while reducing or minimizing the required input power. It is also desirable to reduce the thermal mass of the heaters 105, so that the time required for heating or cooling the system can be reduced.

One design for balancing the above considerations is to use one or more serpentine heaters. If more than one serpentine heater is used, the metal lines for forming the heaters are connected in parallel. For example, FIG. 2A shows a schematic of an RTD integrated on the same chip with the heaters. Various heater configurations have been evaluated mathematically by starting with a heater "y" spacing of 3 mm [See FIG. 2B] and by varying the "x" dimension from 50 microns to 75 microns. This investigation was designed to determine a maximum x spacing allowable between the heater fins. This assists the overall structure in maintaining the desired temperature tolerance of ±1° C. or less, as described above, while also providing increased free space for accommodating an RTD film. The width of the platinum lines was selected to be 150 microns in order to obtain a low overall resistance. FIGS. 3A-D display a set of plots showing the different temperature distributions for different heater spacing. The equation was solved numerically and varied the spacing in the "y" from the edge of the heater relative to the edge of the chip from 100 microns to 200 microns. This produced a temperature variation between +1° C. up to a heater spacing of 70 microns [FIGS. 3A-C]. Increasing the heater spacing beyond 70 microns showed a temperature variation of more than +1° C. [FIG. 3D]. The temperature value was below the +1° C. limit at 105 microns from the lower boundary. Thus, in the embodiment of the invention described above, the 70 micron spacing between the fins of the serpentine heater represents a trade off between heater spacing and the temperature tolerance of a PCR process.

Figure 4A:
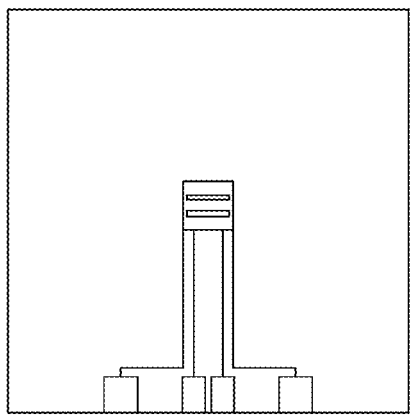
FIGS. 4A-4B depict a structure and corresponding data for a structure according to an embodiment of the invention.
Figure 4B:
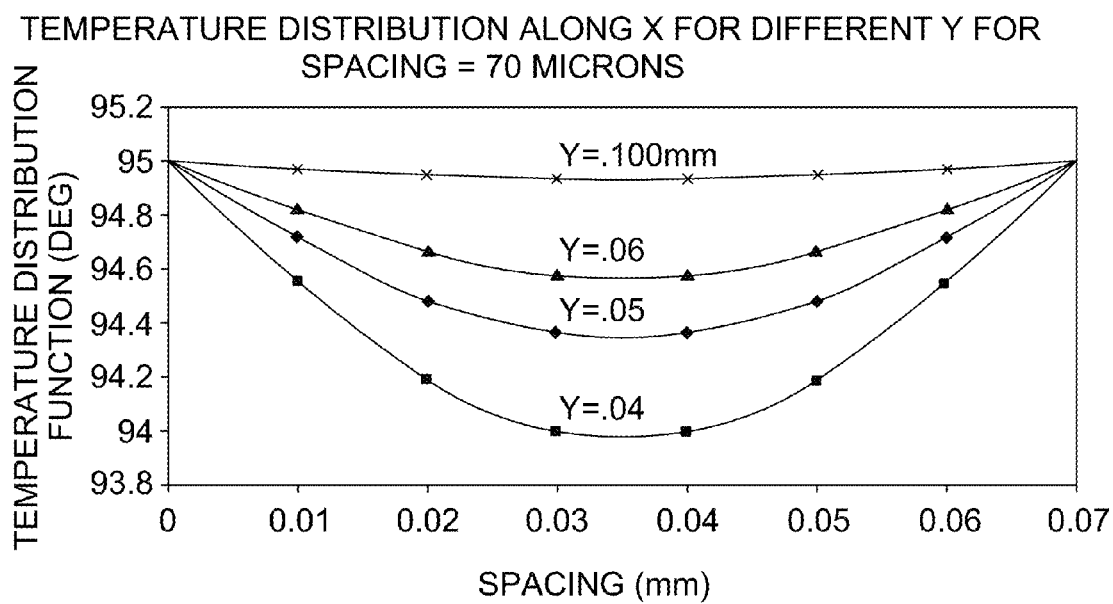

Assuming a 400 nm thickness of the platinum film obtained by sputter coating, the resistance of the platinum heaters calculated was found to be around 350 ohms. The measured 380~400 ohms necessitated the use of higher voltage for the surface temperature of the heaters to rise to 95° C. Operating the chip on a much lower power (~5 W) is desirable for commercial applications. In an effort to reduce the power consumed by the heater, a second heater design was investigated mathematically where the heater was divided into 3 electrical pathways connected in parallel in the same "3 mm×3 mm" area. This parallel combination results in a resistance of around 100~120 ohms. The "y" spacing between the heaters was also reduced to 0.9 mm [FIGS. 4A and 4B]. Once again numerical simulations were performed with a 70 microns "x" spacing for this new "y" spacing value. The heat distribution remained within +1° C. for a y value of 50 microns and above. The temperature distribution curve also achieves a uniform 95° C. value for a "y" value around 100 microns, as compared to 200 microns for the previous serial design. Thus, the parallel design allowed for higher precision control over the temperature distribution as compared to a conventional serial design.

A serpentine heater design according to an embodiment of the invention also provides a reduced thermal mass relative to a continuous thin film heater. For example, for a heater film with a 390 nm thickness, a serpentine heater design such as the one shown in FIG. 2B has a surface area that is ⅔ of the surface area of a continuous film heater. The rate of temperature change (ramp up or ramp down) for the serpentine heater design, however, is 5 times greater than the rate of change for the continuous thin film. As a result, the thermal mass per unit surface area for the serpentine heater is reduced by a factor of 6 relative to a thin continuous film heater.

Other heater designs can be determined by solving a two dimensional steady state heat conduction problem $$(\nabla^2 T = 0), \nabla^2 = \frac{\partial^2}{\partial x^2} + \frac{\partial^2}{\partial y^2}.$$

The temperature boundary conditions for the problem can be selected based on the maximum temperature requirements for a desired amplification method. For example, for an amplification of Infectious Bovine Rhinotracheitis, the boundary conditions can be set to be 95° C. on three sides, which is the maximum temperature required for PCR of the specific genome, and 24° C. (roughly room temperature) on one side.

In another embodiment, the maximum temperature for another PCR reaction could have a different value, such as 90° C. In such an embodiment, the temperature boundary condition changes to having 90° C. on three sides. More generally, the approach described here can be conveniently used to implement a serpentine heater design for any on chip thermal control. The approach provides a maximum inter-fin distance needed for achieving a pre-determined temperature tolerance. The transient part of the heating problem is reduced in importance relative to the requirement of a PCR process is holding the fluid volume at a definite temperature for a certain amount of time independent of the ramp up or cooling rate. The ramping up or cooling rate only provides a time advantage for on chip devices over the conventional counterparts without inhibiting the efficiency of the amplification cycle. A 3 mm×3 mm square area on the silicon surface can be used to fabricate the heaters on the surface of the silicon wafers. Our design involves a RTD (resistance temperature detector) although we performed all testing with a thermocouple at this stage with an intention of integrating the RTD in a future device. Eventually the RTD will be placed in between the serpentine heater path in the design and will be capable of gauging the temperature correctly to the level of +1° C. as desirable for any standard PCR process.

D. Thermocouple

A thermocouple may be incorporated into the PCR amplification system for monitoring the temperature. The thermocouple can be incorporated in any convenient manner. In an embodiment, a thermocouple is formed on the bottom surface of the chip at the same time as the heater. Alternatively, an external thermocouple can be incorporated into the amplification chamber, such as a K type, 5SRTC series thermocouple for sensing the temperature of the chamber. In an embodiment involving an external thermocouple, a hole can be pre-drilled over the chamber in the PDMS. To ensure an interference fit with the hole, the thermocouple can be housed inside a glass tube filled with epoxy such that a small portion of the tip protrudes into the chamber. After the epoxy is cured, the thermocouple is snugly fixed over the PDMS chamber. In such an embodiment, note that the presence of a thin layer of epoxy on the exposed tip of the thermocouple can assist in shielding the tip from interfering with the activity of any polymerase in the chamber. Also, the flexible nature of the PDMS should hold the glass housing tightly, thus enhancing the rigidity of this assembly and reducing or preventing any sample evaporation from the chamber top.

In another embodiment, an RTD (resistance temperature detector) can be integrated with the heaters on the bottom surface of the chip. In such an embodiment, a thin film platinum RTD can protrude into the heaters and can monitor the temperature of the heaters to maintain a desired PCT temperature tolerance. For example, the RTD can protrude around 250 microns into the heaters. Note that in such an embodiment, there will be a time delay between the chamber temperature and the temperature sensed at the RTD. This delay can be calibrated and included in the control software for controlling the heater. Although the device is depicted with a level of ±1 degrees C., the temperature variance level that may be maintained may be any variance including a lower and higher temperature variance. This is discussed in more detail below.

E. Inlet and Outlet Ports

With reference to FIG. 1A, inlet 145 and outlet 150 ports are also provided for introducing a sample into the amplification device and removing a replicated sample. In an embodiment, inlet and outlet ports with plastic caps were fabricated by cutting and polishing the cut ends of standard laboratory PCR vials. The inlet and outlet ports may be tapered. These were mounted over the inlet and outlet reservoirs and used for guiding the PCR mix into the chamber.

II. Method of Fabrication

Figure 1B:
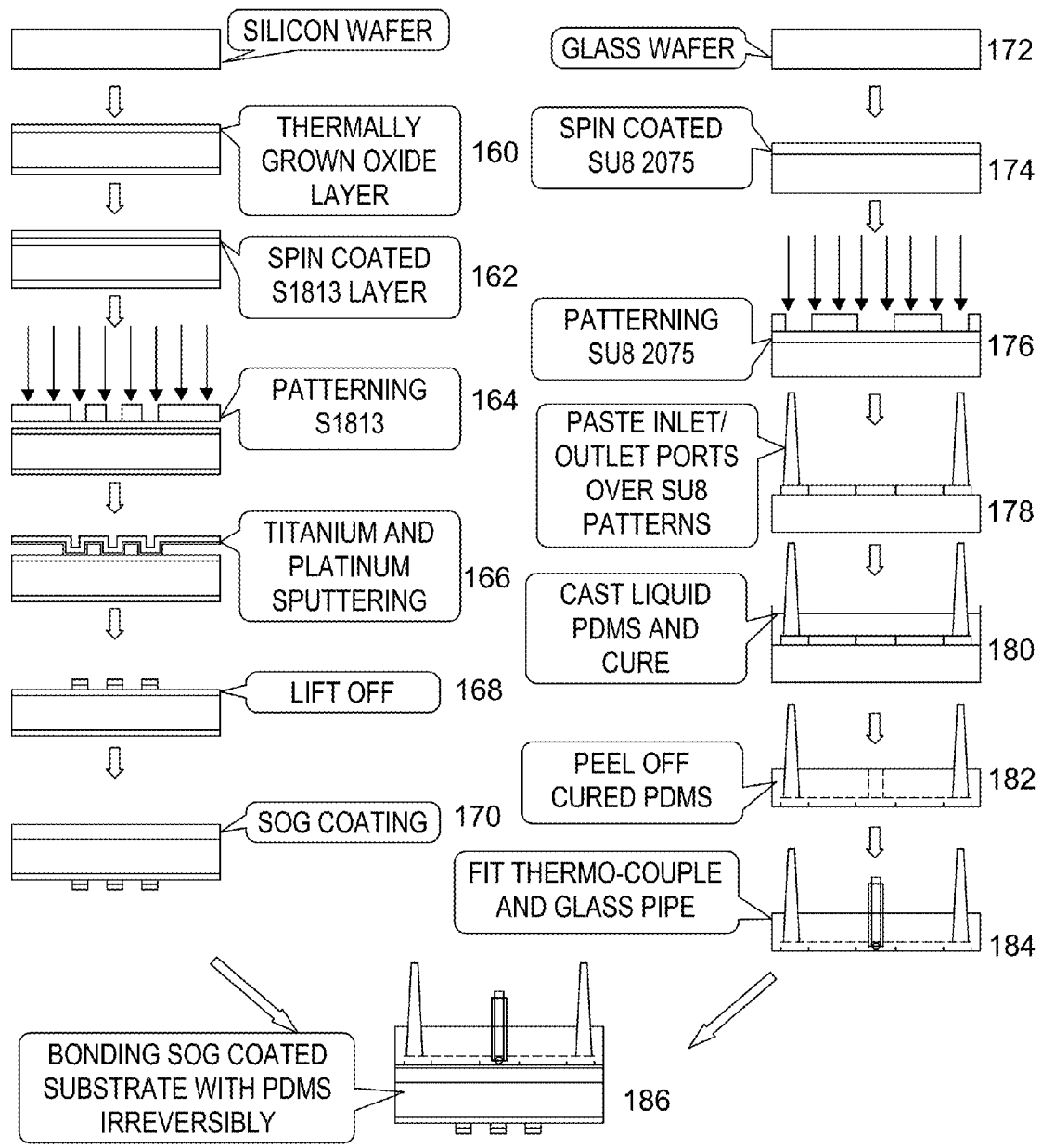
FIG. 1B is a flow diagram of a method for fabricating the device according to an embodiment of the present invention.
Figure 3A:
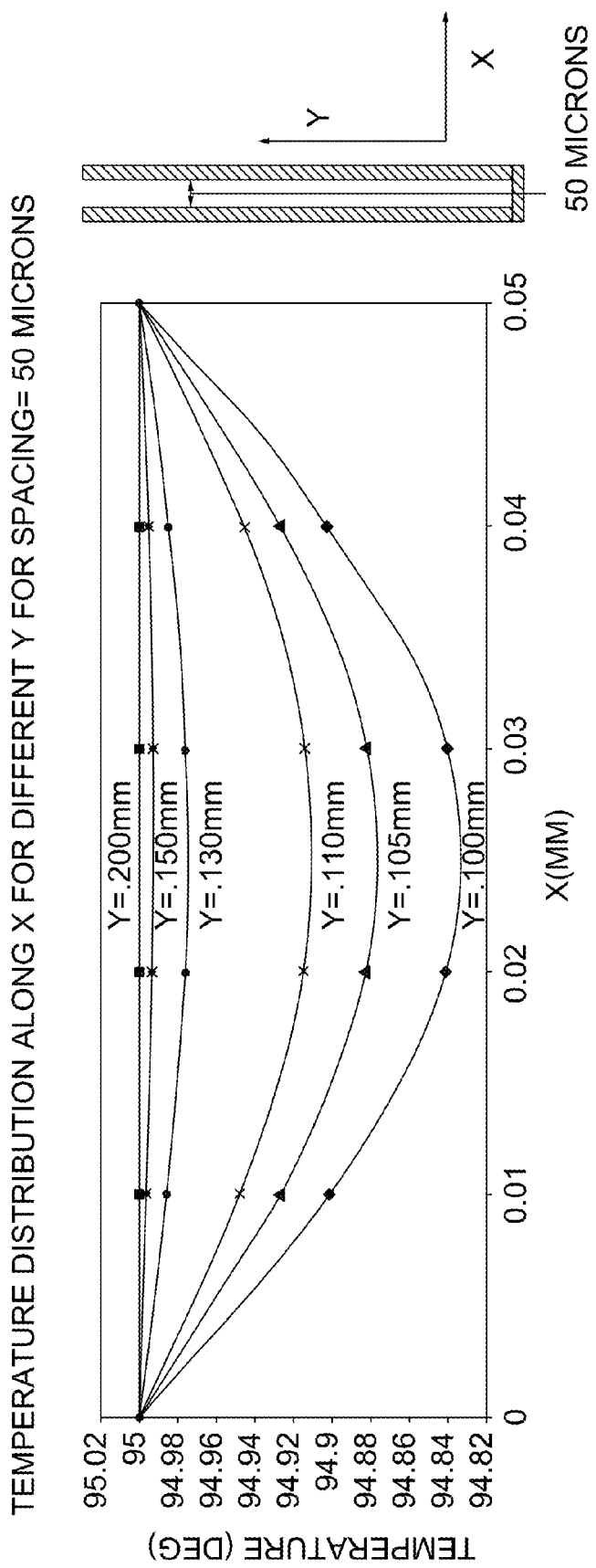
FIGS. 3A-3D depict data collected related to a device according to an embodiment of the invention.
Figure 3B:
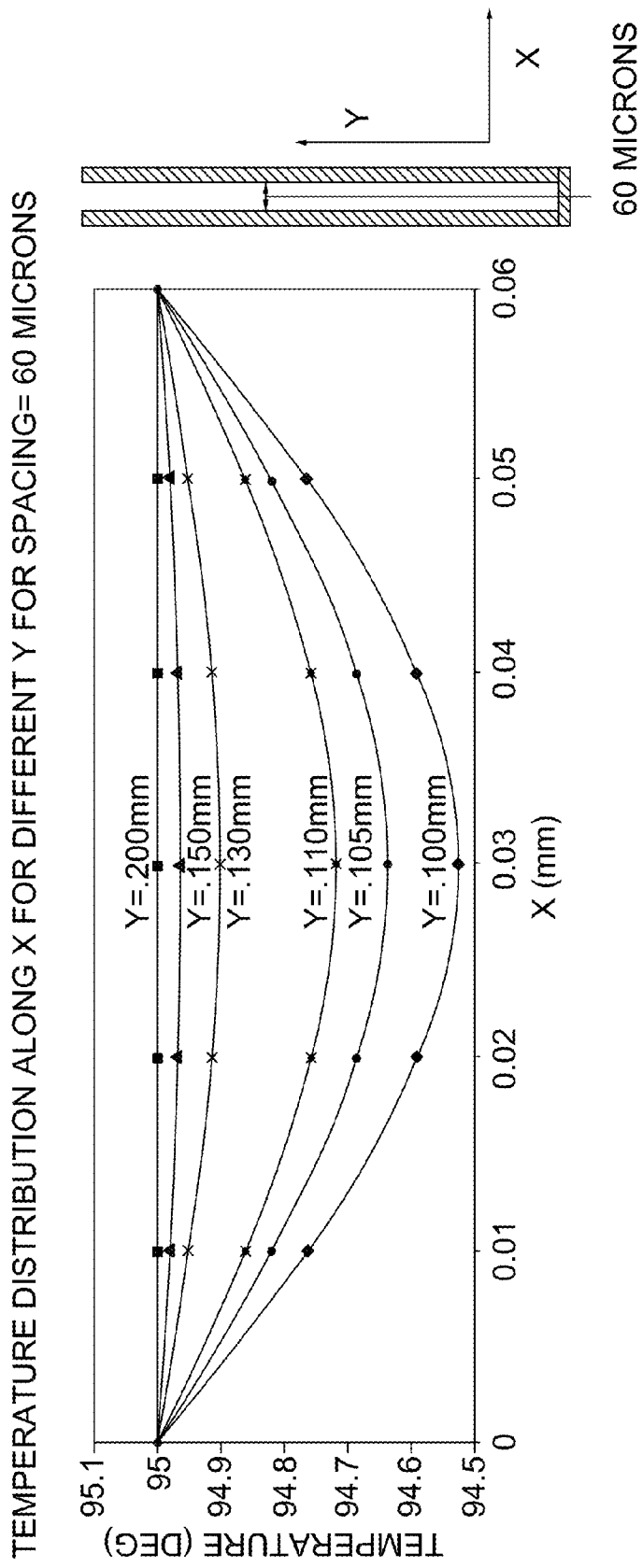
Figure 3C:
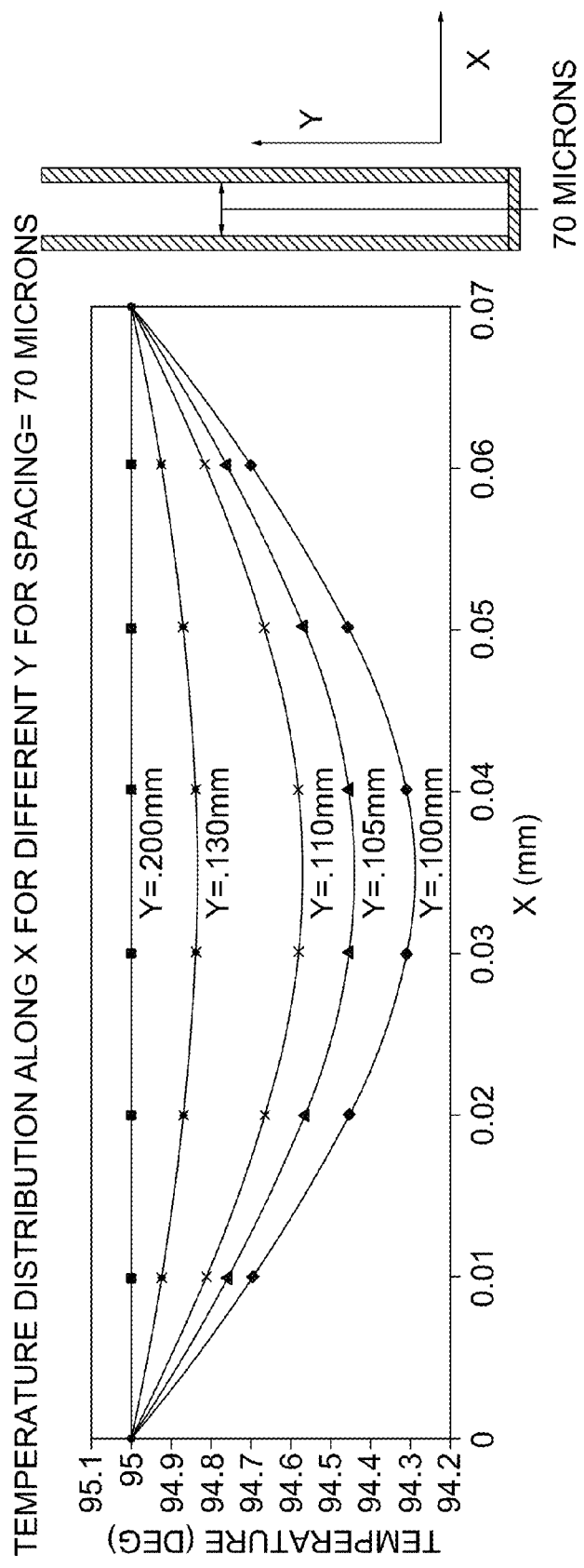
Figure 3D:
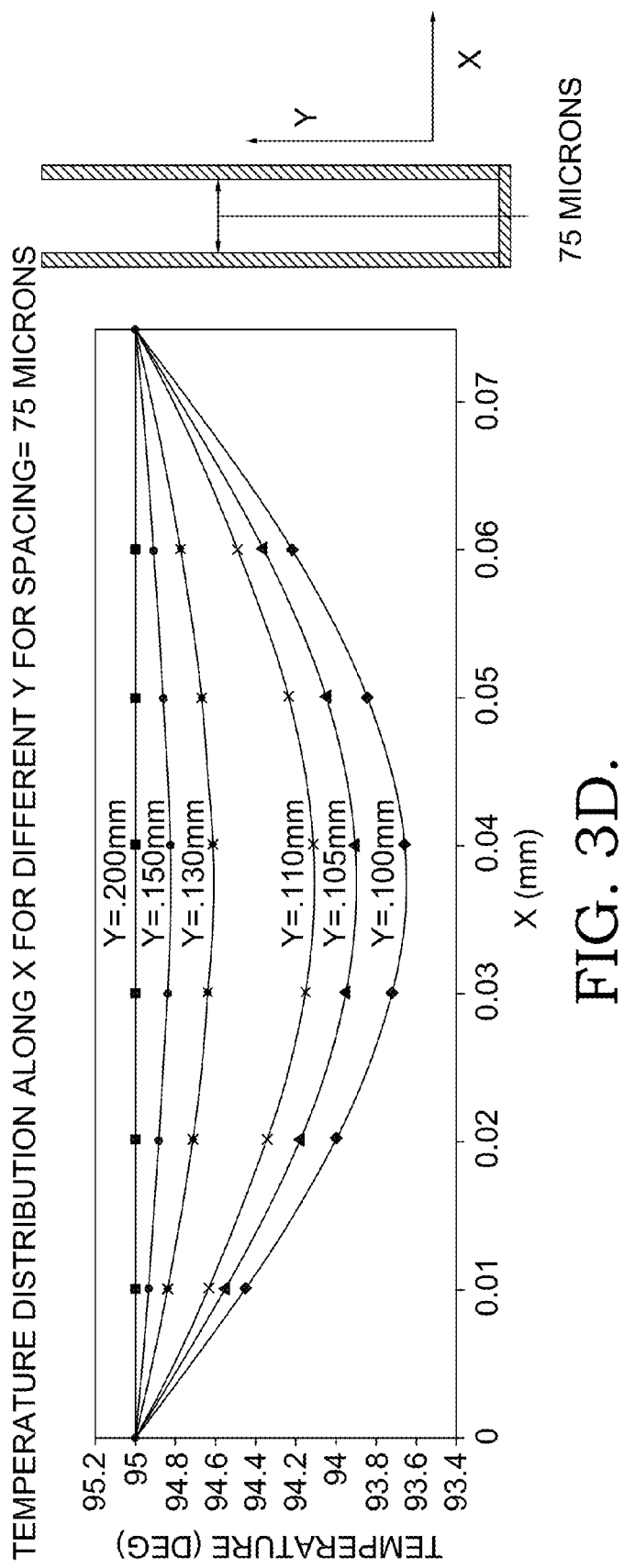

With reference to FIG. 1B, a method for fabricating the polydimethylsiloxane (PDMS) device 100 of FIG. 1A is shown. At step 160, an oxide layer of about 1 micron thickness is thermally grown on the silicon substrate.

At steps 162-168, the heaters are formed by sputtering and liftoff process. At step 162, a photoresist layer is formed on the bottom surface of the silicon substrate. At step 164 the photoresist layer is patterned at step 164 with a desired heater shape. At step 166, the metal of the heater or heaters can be deposited on the patterned photoresist by Argon plasma sputtering or another convenient process. At step 168, the photoresist can then be removed, leading to liftoff of the metal deposited on the photoresist. In an embodiment, the thickness of the metal is at least 250 nm, or at least 250 nm, or at least 400 nm. In another embodiment, the thickness of the sputter deposited metal is 600 nm or less, or 500 nm or less, or 400 nm or less. Preferably, the sputter deposited metal is platinum. In another embodiment, the sputter deposited metal is another metal that is substantially inert. In still another embodiment, the sputter deposited metal layer is composed of multiple metal layers, such as a combination of a layer of platinum with a thin layer of titanium to promote adhesion of the heater to the substrate surface. In yet another embodiment, the sputter deposited metal used to form the heaters can be a multi-layer metal composition. For example, the multi-layer metal composition can include a thin layer of titanium to promote adhesion, a thicker layer of aluminum on the titanium, and a thin layer of platinum on the aluminum. This type of deposition scheme provides a reduced fabrication cost, as the majority of metal material can be aluminum, which is cheaper than platinum. In such an embodiment, platinum provides an inert cover for the aluminum. Note that if an inert cover is not used on top of the aluminum and the aluminum is allowed to be exposed to air, the aluminum will be susceptible to oxidation during the rapid heating and cooling cycles associated with PCR processes. Such oxidation would lead to increased resistance for the aluminum film.

After deposition, the metal lines used to form the heater can be annealed. The annealing can represent a separate process, or the annealing can occur during an annealing step for another portion of the amplification device. Preferably, the metal lines are annealed at a temperature of at least 250° C. or at least 350° C. In another embodiment, the anneal temperature is 500° C. or less, or 400° C. or less. The anneal time can be at least 10 minutes, or at least 20 minutes, or at least 30 minutes, or at least 40 minutes.

A heater may be made by using photoresist as a masking layer to deposit a 20 nm layer of titanium followed by a 400 nm of Platinum. The metal layers were deposited using a sputter coating system manufactured by Emitech (K-575X) UK. The photo-resist was removed by ultra-sonication in acetone to leave the metallized pattern on the surface. A 20 nm layer (150 mapms, 110 secs) of Titanium and a 390 nm layer of platinum (90 mapms, 12 mins.) were then deposited at a chamber pressure of $10^{-4}$ mbar. The temperature of the heater lines was measured by contacting various areas of the heater with a thermocouple tip and was seen to vary from 70°-C. in the thick portions to 114°-deg. C. in the thin portions.

Continuing the method of FIG. 1B, at step 170, the surface of the silicon wafer opposite to the heater structures is spin-coated with a layer of spin-on glass (SOG). A spin-on glass layer is deposited by depositing a flowable precursor onto a wafer containing the chip and then spinning the wafer to produce an even thickness of the SOG over the wafer. One commercially available SOG is available from Filmtronics.

Several different rotational speeds (such as 6000, 8000 and 10,000 rpm) were tested in order to produce different thicknesses. The SOG coating was then temperature cycled on a hotplate in a conventional manner, such as according to the manufacturer specifications, to form a solid layer. For example, the SOG can be temperature cycled through four steps of temperature in a nitrogen atmosphere. In such an embodiment, the steps can include 150° C. for 1 min., 180° C. for 1 min., 250° C. for 1 min. and 400° C. for 30 mins on a hot plate. The thicknesses generated at various rpms were further confirmed by ellipsometric measurements and found to be 564 nm, 406 nm and 140 nm respectively. More generally, thicknesses between 1340 nm and 140 nm were obtained at various rotational speeds between 1,000 rpm and 10,000 rpm. The temperature difference between the lower and upper surfaces of the chip was determined using two thermocouples, one over the heater face and the other over the SOG coated face. A preferred thickness range for the SOG is between 140 nm and 450 nm in order to reduce or minimize the temperature difference between the heaters and SOG surface while providing desirable structural properties for bonding of a PDMS layer on the SOG surface. Preferably, the thickness of the SOG is selected to maintain a temperature difference between the lower and upper surfaces of 2° C. or less.

At steps 172-184 of FIG. 1B, the PDMS layer is fabricated with channels and chamber. In an embodiment, the PDMS channels and other structures can be fabricated by making a photoresist mold, such as a negative photoresist mold, using a multi-layering process on a glass or silicon wafer with standardized lithography and replica molding. For example, masks can be made using Adobe Illustrator and a 3000 dpi printer on a transparency film. In order to achieve 450 micron thick photoresist features, two layers of photoresist coating can be used, with each layer being cured according to the manufacturer's specifications prior to the next layer deposition and/or other processing step. Additionally, a multi-layering process can be used to fabricate thick SU8 structures which are useful for a variety of microfluidic maneuvering, such as pumping or valving.

In an embodiment, a PDMS structure can be formed by forming a negative of the desired device using photoresist, with the patterned photoresist defining the desired channels, chambers and reservoirs for inlet/outlet ports. This negative can then be used to cast a device using the silicone elastomer poly(dimethyl)siloxane (PDMS) (GE Silicones RTV 615). The PDMS rubbery slab with imprints of the channel, chambers and reservoirs is then separated from the SU8 mold.

In an exemplary embodiment, PDMS channels were fabricated by making a mold using the negative photoresist SU8-2075. The SU8-2075 photoresist is relatively thick in comparison to other conventional photoresists. The SU8 photoresist mold was formed on a glass or silicon wafer with standardized lithography and replica molding. Masks were made using Adobe Illustrator and a 3000 dpi film printer. The SU8-2075 photoresist was spun onto a 25.4 mm×25.4 mm glass wafer. The photoresist was spun at 1000 rpm to obtain a thickness of 225 microns and then cured using a two temperature heating process. Another layer of photoresist was spin-coated on the top of this cured layer to obtain an overall thickness of around 450 microns. This layer also experienced the same curing cycle. The SU8 was patterned lithographically, by exposure to a UV light source through another black and white transparency printed at 3200 dpi resolution. Upon such exposure, and subsequent heating, the SU8 formed extensive cross-links, and became chemically resistant. The areas screened by the black portions of the mask did not cross-link, and could be dissolved by a chemical developer (SU8 nano developer, M/S Microchem) that did not affect the exposed areas. Thus, a negative of the desired device was obtained, with SU8 features defining the desired channels, chambers and reservoirs for inlet outlet ports. This negative was used to cast a device out of the silicone elastomer poly (dimethyl)siloxane (PDMS) (GE Silicones RTV 615). The glass negative was placed at the bottom of a plastic case, which was then filled to a depth of 1.5 mm with PDMS. The case was then carefully placed on a flat bench in a vacuum oven and degassed for 45 mins. This was followed by curing the PDMS at 80° C. for 45 minutes.

Prior to bonding the PDMS imprint onto the SOG layer at step 186 of FIG. 1B, the bonding surfaces of both the PDMS and the SOG are exposed to an oxygen containing plasma in a plasma etcher. The goal of the oxygen plasma treatment is to reduce the contact angle of both the PDMS and SOG prior to bonding. A range of values for the plasma parameters a) RIE power; b) Chamber pressure; and c) Time of exposure can be used to produce a desirable contact angle. Preferably the contact angle for both the PDMS and the SOG after plasma exposure is less than 10 degrees, or less than 7.5 degrees, or less than 5 degrees. In an embodiment, the plasma power can be at least 5 W, or at least 10 W, or at least 20 W. In another embodiment, the plasma power can be 25 W or less, or 20 W or less. In an embodiment, the chamber pressure can be at least 750 mTorr, or at least 800 mTorr, or at least 850 mTorr, or at least 900 mTorr. In another embodiment, the chamber pressure can be 1050 mTorr or less, or 1000 mTorr or less, or 950 mTorr or less, or 900 mTorr or less. In an embodiment, the time of exposure to the plasma can be at least 25 seconds, or at least 30 seconds, or at least 35 seconds. In another embodiment, the time of exposure can be 45 seconds or less, or 40 seconds or less, or seconds or less.

After exposing the SOG coated wafer and the PDMS structure to the oxygen plasma, the SOG wafer and PDMS structure should be bonded together relatively quickly at step 186 of FIG. 1B. After plasma exposure, both the SOG wafer and PDMS structure will have a relatively low contact angle. This is believed to correspond to a reduced density of methyl groups at both surfaces and an increased density of hydroxyl groups. At this low contact angle, the two surfaces will join together with an increased bonding strength relative to SOG and PDMS surfaces joined together with no plasma exposure or a less desirable plasma exposure. Over time, both the SOG surface and the PDMS surface will show an increased contact angle, which is believed to be due to a return to greater amounts of exposed methyl groups and reduced numbers of exposed hydroxyl groups.

Figure 5A:
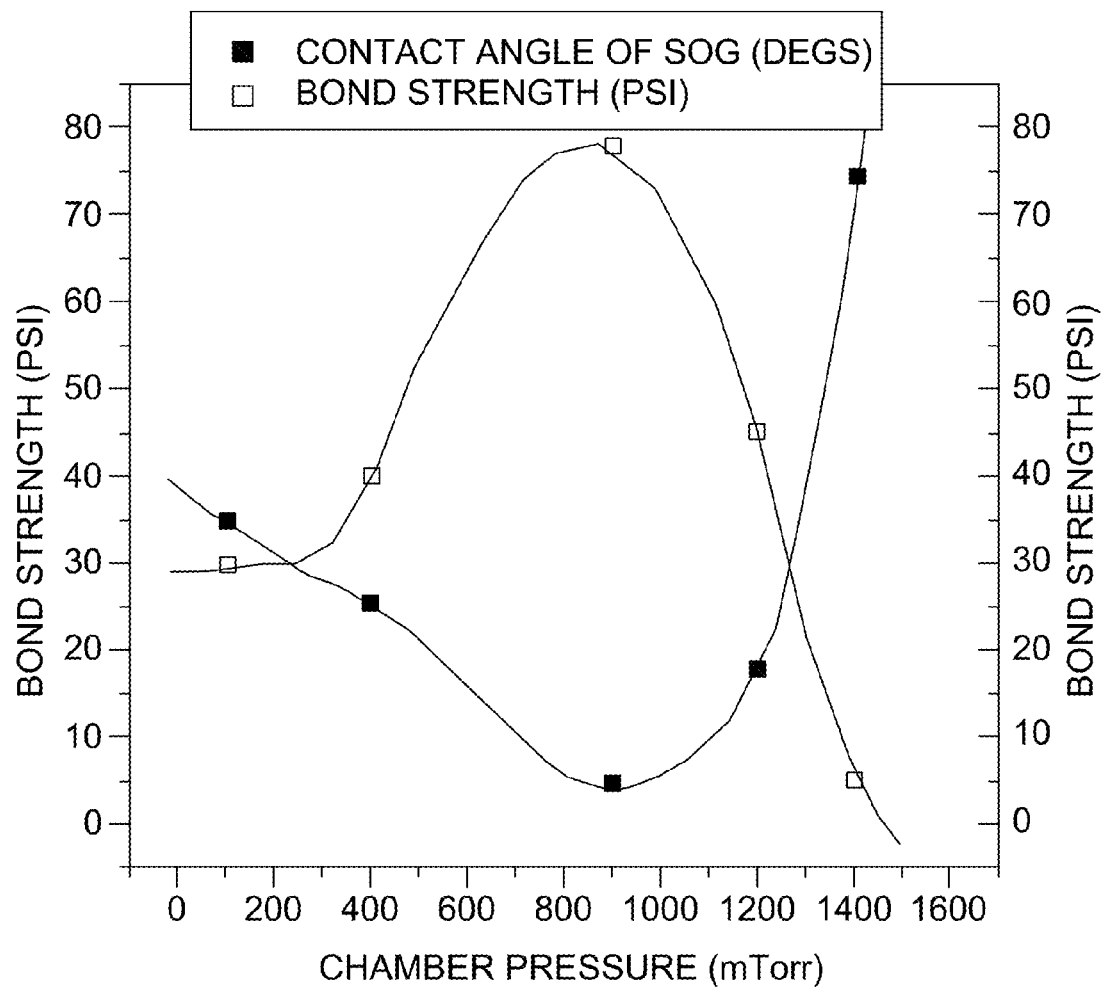
FIGS. 5A-5C depict data collected related to a device according to an embodiment of the invention.
Figure 5B:
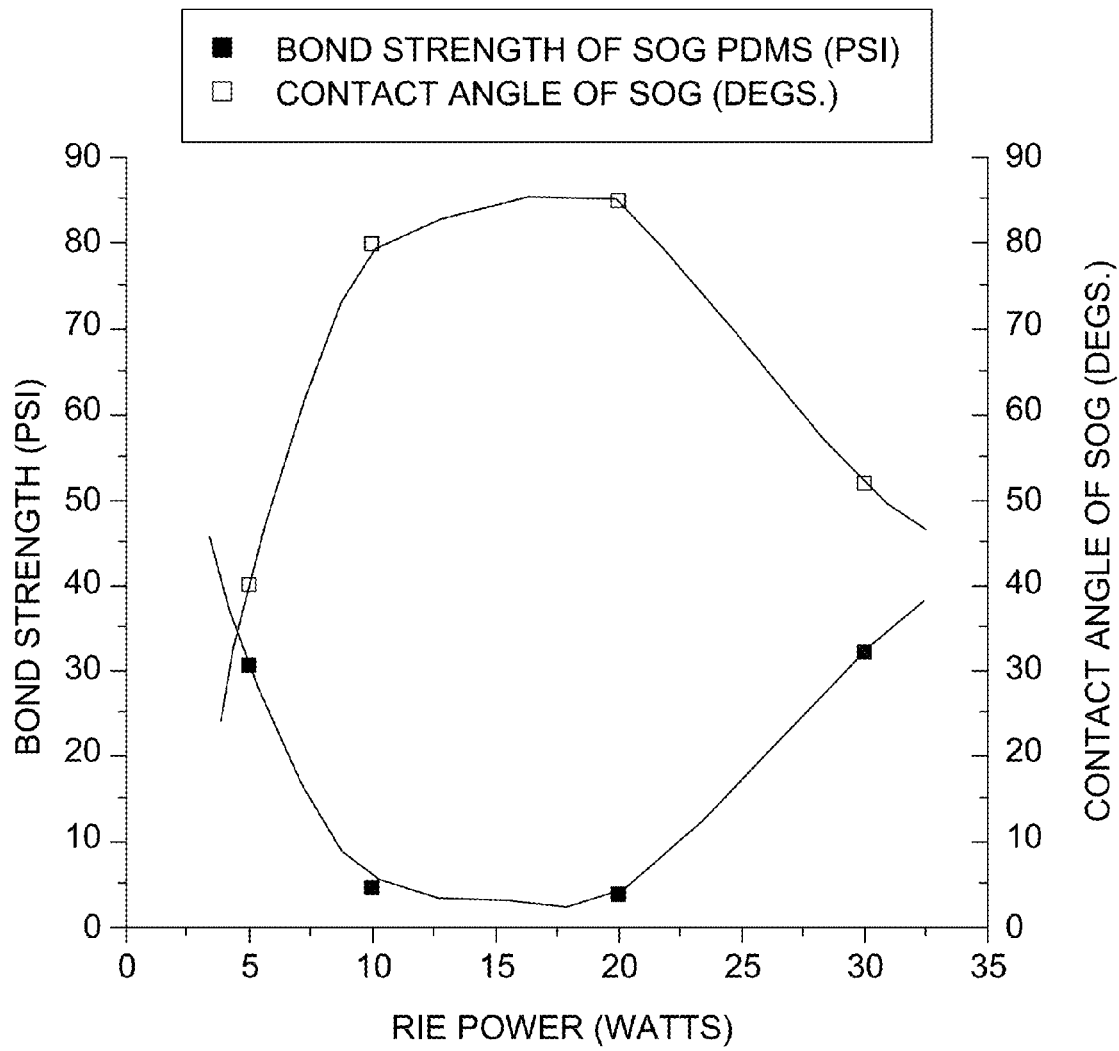
Figure 5C:
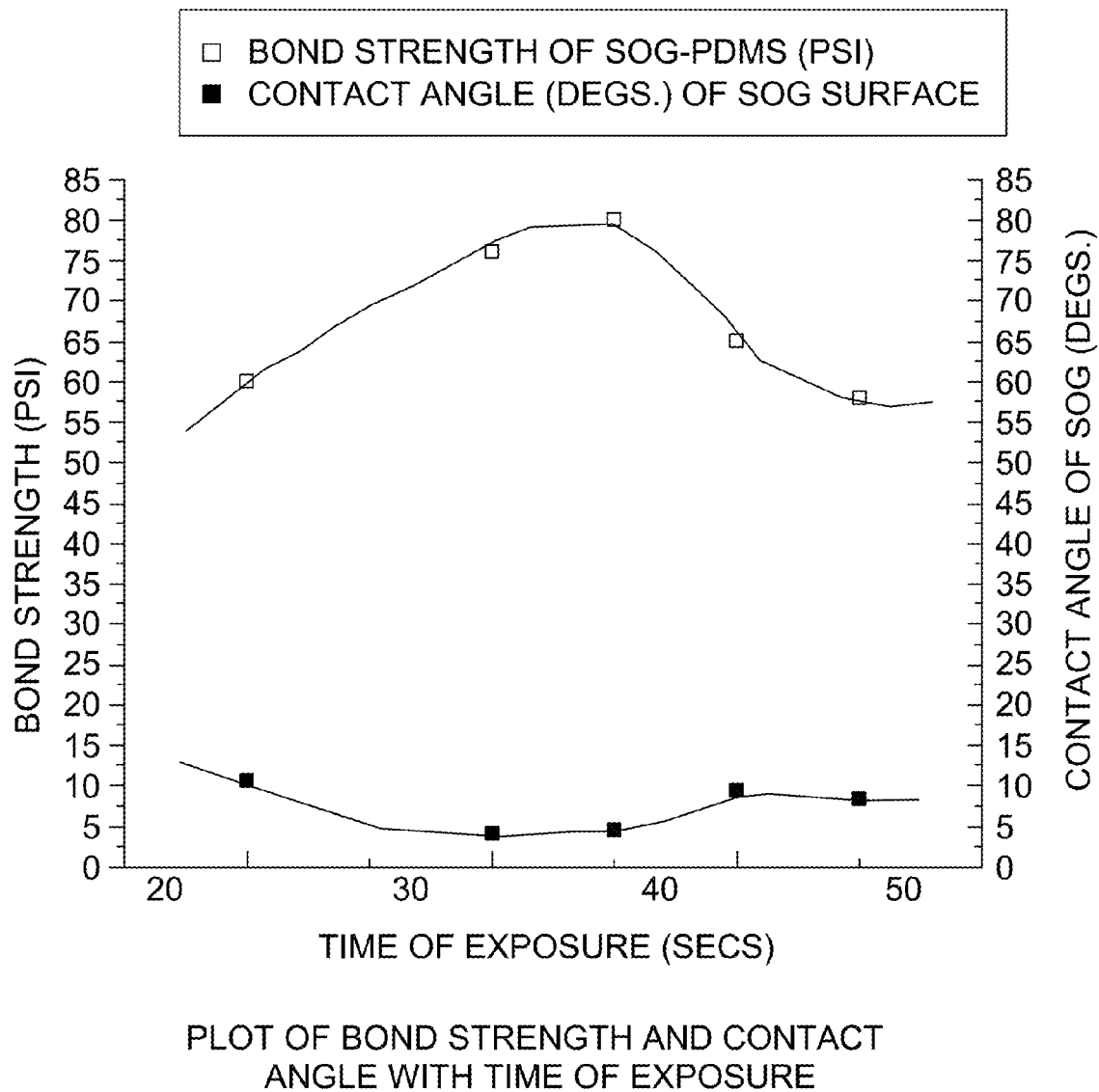

FIGS. 5A, 5B and 5C demonstrate the impact on bonding strength and contact angle for SOG and PDMS surfaces when different plasma parameters are varied, such as chamber pressure, RIE power, and time of exposure. As shown in the curves, reducing the contact angle of the SOG and PDMS surfaces results in increased bonding strength. For example, FIG. 5C shows an example of how changes in time of exposure to the oxygen plasma impact the contact angle and bond strength for SOG and PDMS surfaces. As shown in the figures, the contact angle approaches a minimum for plasma exposure times near 25-45 seconds. Correspondingly, the bond strength of the SOG-PDMS bond increases as the contact angles approach a minimum.

Figure 6:
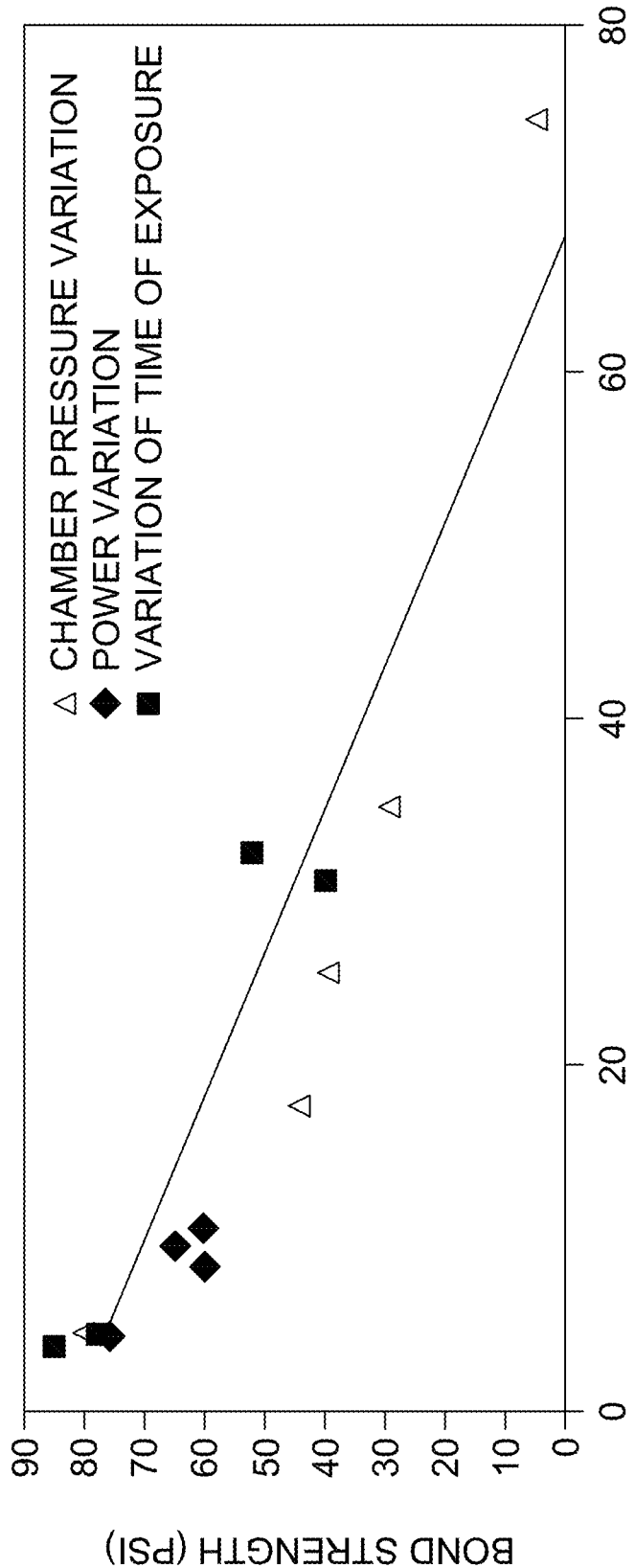
FIG. 6 depicts data collected related to a device according to an embodiment of the invention.

FIG. 6 demonstrates the universal curve between bond strength and contact angle plotted on the data set obtained during variation of individual plasma parameters. The data in FIG. 6 show a linear curve of best fit between the bond strength and the contact angle data. The intercept values at both of the axes correspond to different conditions. The intercept at the x-axis indicates an unexposed surface with "0" bond strength. Correspondingly, the intercept at the y-axis indicates a maximum bond strength when all the surface methyl groups have been removed. The x intercept closely matches the contact angle value for an unexposed surface. A general methodology of estimating bond strength has been developed for all surfaces which undergo hydroxylation when exposed to oxygen plasma. A universal curve can be plotted for a pair of all such substrates, and this can be used to predict the bond strength values. For a desired combination of bond strength and contact angle, the parametric variation curve [such as the curves shown in FIGS. 5A-C] can be referred to in order to determine the exposure conditions that will produce the desired combination.

III. Thermal Cycling System

Figure 7A:
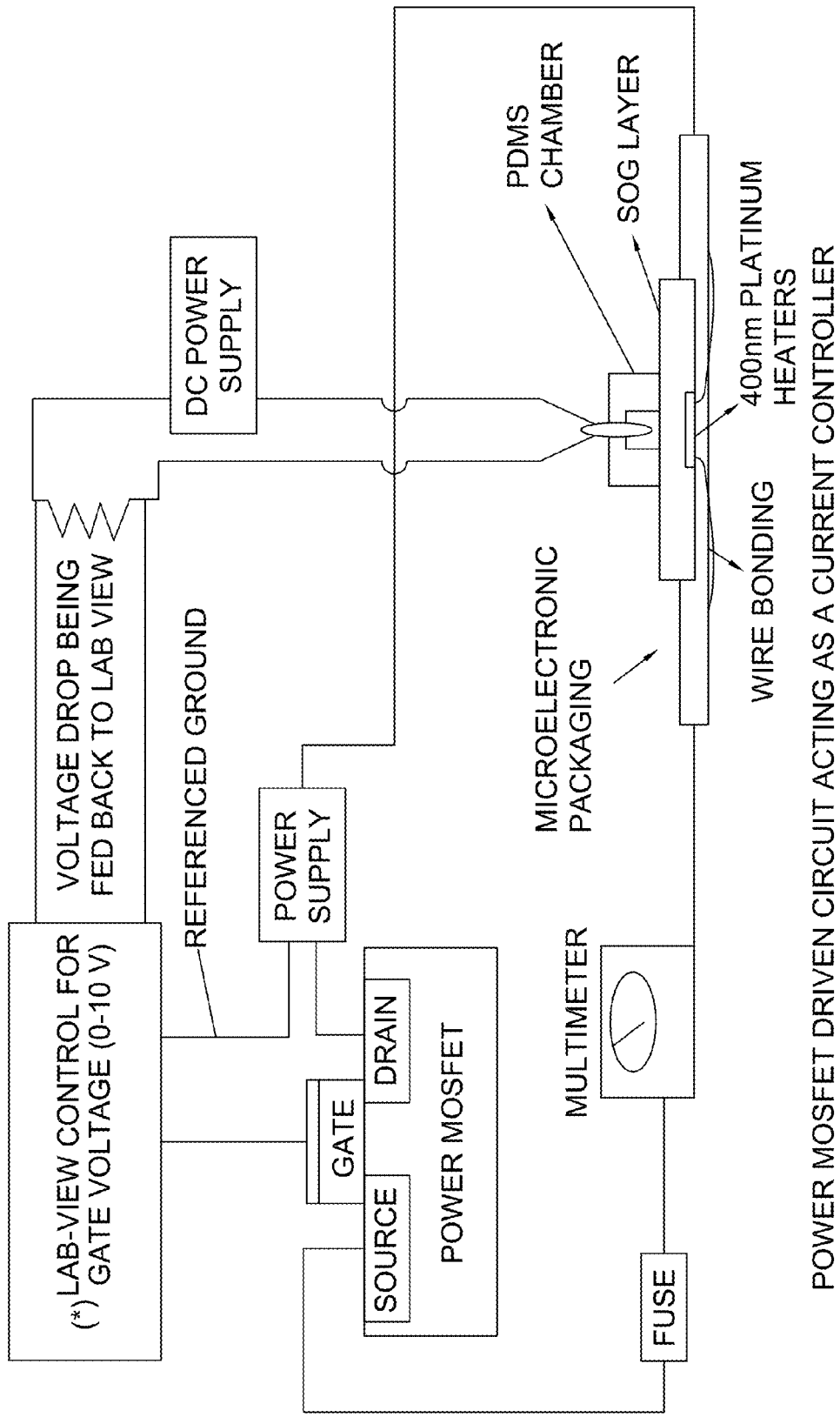
FIGS. 7A-7B depict a structure and corresponding data for the structure according to an embodiment of the invention.
Figure 7B:
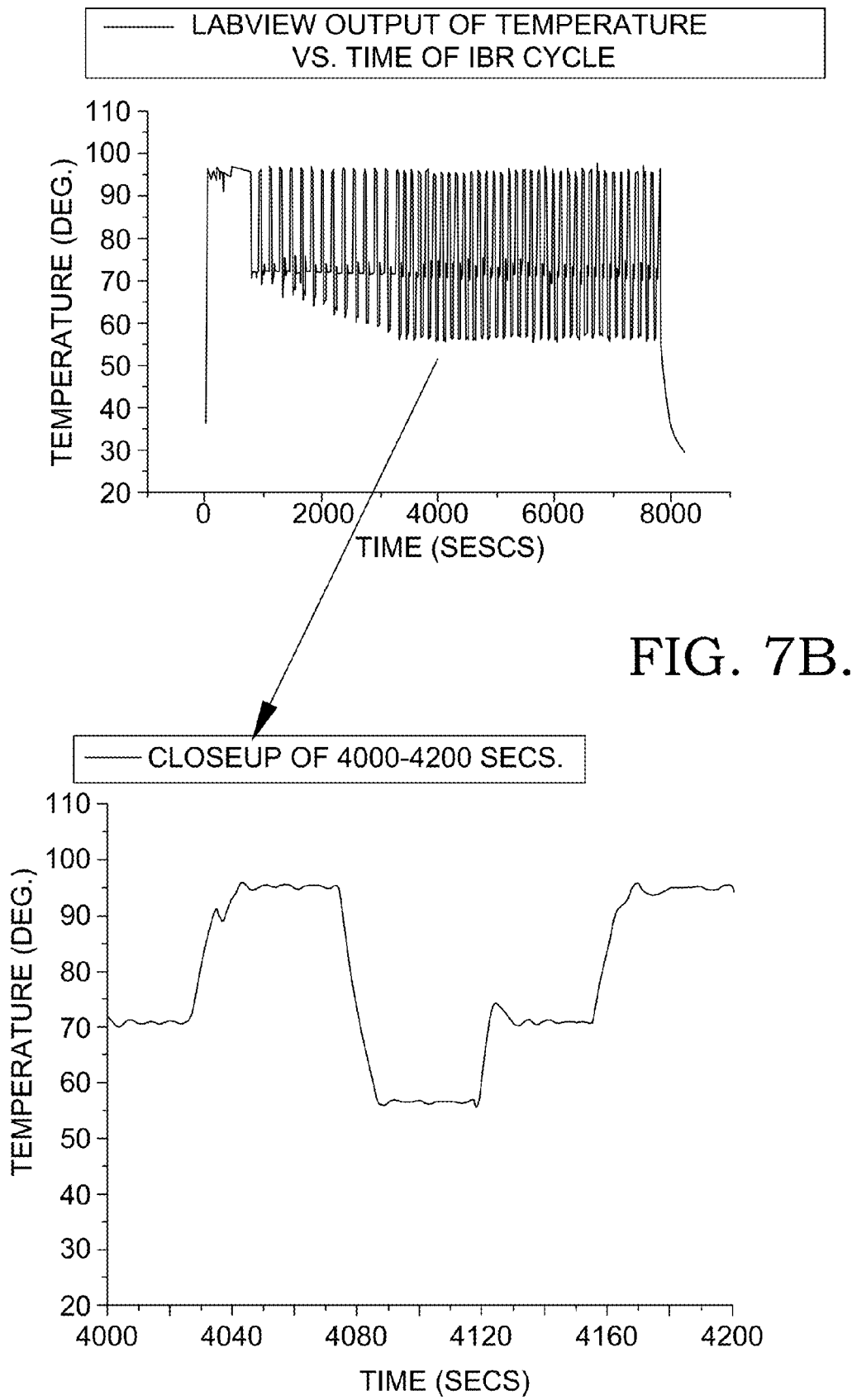

In an embodiment, the heaters for the amplification system can be controlled using an automated thermal cycling system. An example of software for controlling an automated thermal cycling system is National Instrument's Lab-view software. The control is executed by a current controller with a power MOSFET serving as a PWM (Pulse Width Modulation) device by varying the duty cycle of the gate voltage as a switch. FIGS. 7A and 7B show the circuitry and the real time plot of one complete PCR cycle. The IBR cycle details are enumerated in FIG. 11. The thermal cycle control is executed by a PID controller programmed in Lab-view. The input of the PID controller is the voltage output from the thermocouple junction and the output is a continuous 100 Hz pulse train with varying duty cycle depending on the difference between the temperature set point and instantaneous thermocouple reading. This pulse train is fed to the gate of the power MOSFET to control the heating power as PWM. The number of cycles in a certain PCR and temperature set point of different cycles can be flexibly changed in the program. The cycle data is in a 2-D array format, which allows the temperature and time values can be easily changed to obtain a universal program for any PCR cycle. The entire IBR cycle is programmed as a time temperature matrix, which executes the cycle by reading the control array. The full IBR cycle normally takes 270 mins in a conventional setup. The total cycle time realized by adding up all the hold times at the various temperature states is 115 mins. The remaining 155 mins are spent in a conventional thermocycler to ramp the temperature up and cooling down of the huge metal block sample vial holder. As indicated in FIG. 7B the total IBR cycle takes around 129 mins in the on-chip setup, of which 115 mins are realized in hold times. The ramp up and down times add up to around 14 mins which is reduced by a factor of 10 from that of the conventional system. The time differential between a conventional thin continuous film design and a serpentine design according to an embodiment of the invention was also investigated. Results of this experiment also indicate a 5 time reduction in ramp up and down times at low input powers. This makes designs according to embodiments of the invention highly portable, as the designs can be run with 6 W of power or less.

In some embodiments, the PCR amplification device can be a reusable device. In such embodiments, after a first amplification, the chambers of the amplification device can be cleaned prior to a second use, such as by washing with water or a standard PCR buffer solution such as PCR buffer 1×TAE or 1×TBE. In order to introduce a cleaning fluid into the PDMS chambers, a peristaltic pumping system can be incorporated into the device.

IV. Reusable Device

Figure 8:
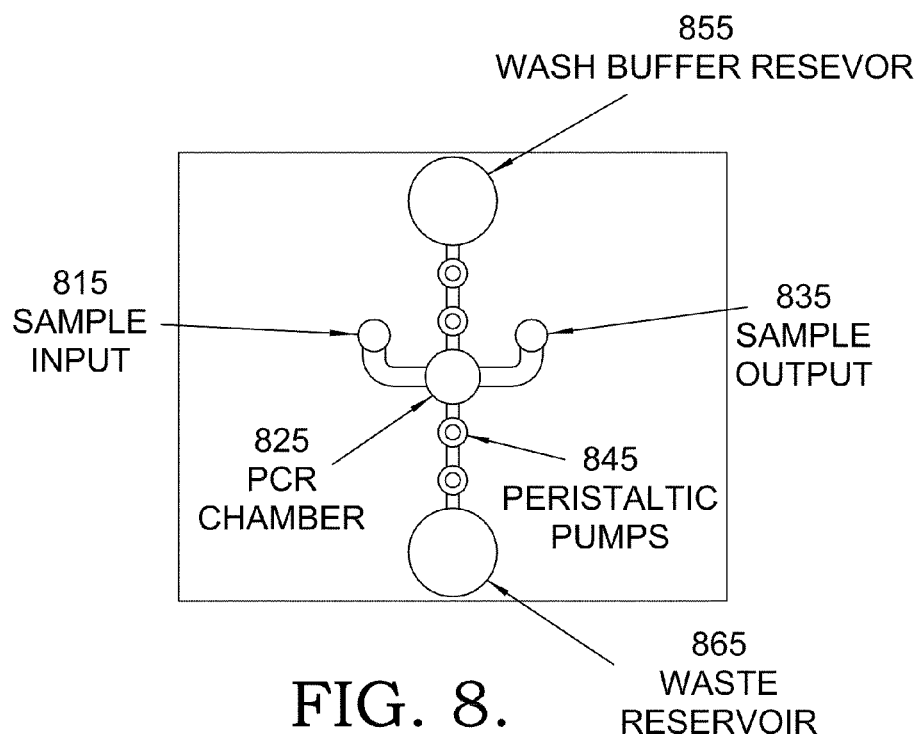
FIG. 8 depicts a structure according to an embodiment of the invention.

FIG. 8 provides a schematic of a peristaltic pumping device according to an embodiment of the invention. In FIG. 8, a sample can be introduced into PCR chamber 825 through sample inlet 815. The sample inside the PCR chamber 825 can be extracted via sample outlet 835 using a hypodermic syringe. Peristaltic pumps 845 are positioned orthogonally to the path of sample inlet 815 and sample outlet 835. The peristaltic pumps 845 allow the inlet 815, PCR chamber 825, and outlet 835 to be washed by circulating the TAE and TBE buffer solution from buffer reservoir 855 to waste reservoir 865.

Figure 9A:
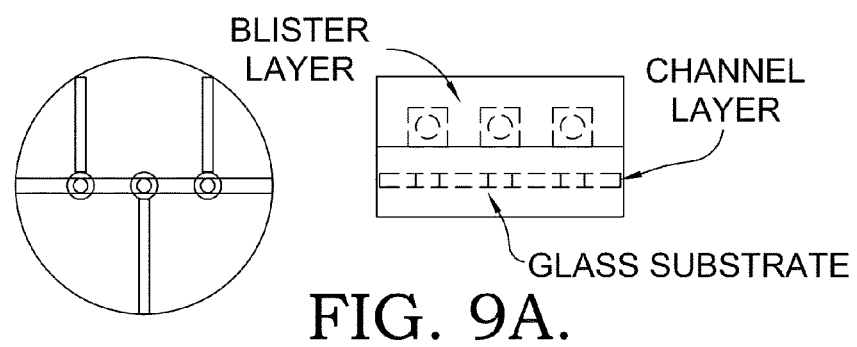
FIGS. 9A-9C depict a pumping structure and corresponding pumping cycles according to an embodiment of the invention.
Figure 9B:
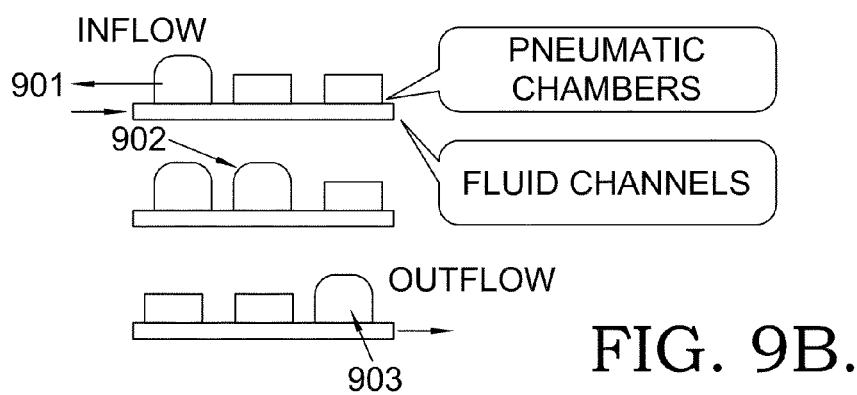
Figure 9C:
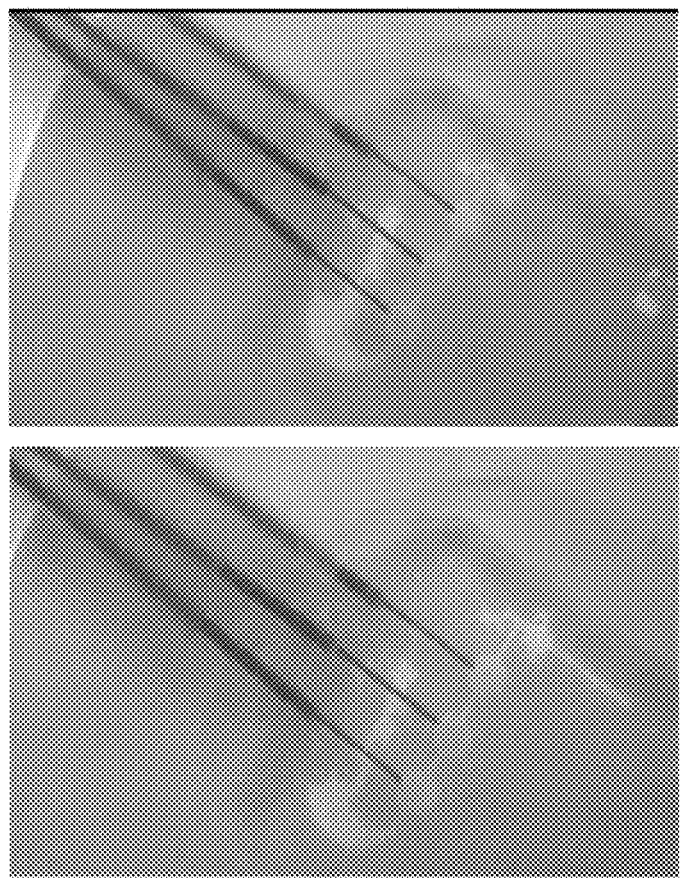

FIGS. 9A and 9B show an example of a peristaltic pump and corresponding pumping cycle. In an embodiment, the pump is realized in three layers: the first layer forms the support base, the second layer forms a channel layer in PDMS, and the third layer forms the blister pockets in the PDMS. The channel layers have a set of pumping chambers placed immediately below the blister pockets in the top layer. The blisters are connected to a compressed air cylinder through a set of solenoid controlled gating valves. The valves are operated in a predetermined and programmed sequence. For example, another Lab-view code can be used to control the solenoid action electrically. In the embodiment shown in FIGS. 9A and 9B, the pumping cycle is initiated by pumping the buffer solution out of the buffer reservoir situated in the channel layer into the first peristaltic chamber 901. The buffer solution can be forced or pumped out of the reservoir by deflating the top mounted blister over the first peristaltic (pump) chamber 901 and expanding the reservoir situated underneath the blister in the channel layer. The first peristaltic chamber 901 expands upon receiving the buffer solution. The first peristaltic chamber 901 can then be compressed, such as by using a compressed nitrogen supply, to force the buffer solution to flow into second peristaltic chamber 902. At this point, the pressure on the initial reservoir can be removed, as the pressure on first peristaltic chamber 901 will prevent backflow. Second peristaltic chamber 902 can then be compressed to force fluid flow into third peristaltic chamber 903. Those of skill in the art will recognize that this pumping cycle can be repeated as necessary to translate a solution through a series of chambers. Additionally, the fluid can be maneuvered bi-directionally by simple inversion of the expansion/compression sequence. FIG. 9C shows Span-shots of a fluorescence dye flowing through the micro-channel taken at 4 second intervals.

In an embodiment, a reusable chip could be used for multiple PCR processes in a method similar to the following hypothetical example. First, a reusable amplification device having a washing capability is provided, such as an amplification device having peristaltic pumps for delivering a wash buffer solution. A first DNA solution is introduced into the amplification device. A PCR process is then performed to using the temperature control and cycling mechanism to amplify the DNA. After amplification, the DNA is extracted from the amplification chamber using a hypodermic syringe. The chambers in the amplification device are then washed with a buffer solution. Because of the surface recovery mechanism for the SOG and PDMS surfaces as described above, the walls of the chambers in the amplification device do not bind strongly with DNA. As a result, the chambers are relatively easy to wash. After washing, the chambers are exhausted by transferring the washing solution into a waste reservoir. A second DNA sample can then be introduced into the amplification device. This second DNA sample is amplified using its corresponding time and temperature matrix and then also extracted with a syringe. During the second replication process, the second DNA sample is not contaminated with left over DNA from the first DNA sample, or any other previous samples. Because of the high contact angle surfaces that form the amplification device (SOG and PDMS), the wash solution is effective in removing any residual DNA left behind during the first amplification. In other words, residual DNA does not bond effectively to the surfaces and is left free due to the non-wetting nature of the surfaces. Note that the high contact angle surfaces are due to the recovery properties of SOG and PDMS surfaces after exposure to oxygen plasma as noted above.

In still another embodiment, the replica molded PDMS structure can also include components for performing a gel electrophoresis on chip as well as optical detection of the electrophoresed stains on the same chip using a fluorescence collection and readout mechanism. For example, optical waveguides can be incorporated into the molded PDMS structure to carry a fluorescence signal from an on chip detection system to a display device, such as a spectrophotometer. A set of on chip light emitting diodes mounted at pre-calibrated locations over the gel channel can be used to excite the post-electrophoresed DNA stains as obtained in the gel channel. In order to achieve the index of refraction differences necessary for realizing a waveguide, the PDMS can be doped with a substance such as $TiO_2$. Further, normal capillary gel electrophoresis takes a high voltage which is not practical for field applications.

V. DNA Amplification Methods

In an embodiment, an on-chip PCR reaction can be carried out using a PCR amplification kit, such as the HotStart Taq, DNA polymerase kit from Qiagen. In an exemplary embodiment using the amplification kit, 20 µl of PCR mix was prepared by mixing 2 µl of 10× buffer, 0.4 µl of dNTP, 0.1 µl of TAQ, 15.5 µl RNase free water, 1 µl of primer and 1 µl of sample. This was thoroughly mixed in a Fisher Vortex Genie 2 mixer. The sample was centrifuged and 5 µl was amplified in a standard Perkin Elmer PCR machine. For the PCR on a chip device, 6 µl was put through the inlet port into the channels and chamber. Mineral oil was put in both ports in equal quantities for sealing evaporation, and capping of the plastic ports was performed to prevent any sample evaporation.

In another embodiment, Infectious Bovine Rhinotracheitis (IBR) virus was used as a test assay for on chip studies. An IBR test assay was used due to the long thermal cycling time, which allows for evaluation of the reliability of a device. The IBR virus test assay also provides a strong fluorescence response of the viral genome in any standard laboratory gel setup which facilitates the replicability of the detection process. Standards and diluted samples of a 527 by target region in the IBR viral genome, which is a form of herpes virus, have been successfully amplified. Samples of PRRS (porcine reproductive and respiratory syndrome retrovirus) have also been amplified.

The IBR virus was originally recognized as a respiratory disease of feeder cattle in the western United States during the early 1950s. The IBR virus can persist in a clinically recovered animal for years as it remains inactive and "hidden" following an infection and is thought to be re-activated by stresses applied to the animal. The virus that causes IBR is capable of attacking many different tissues in the body and, therefore, is capable of producing a variety of clinical disease forms depending on the infected tissue. The clinical diseases caused by the IBR virus can be grouped as (1) respiratory tract infections, (2) eye infections, (3) abortions, (4) genital infections, (5) brain infections, and (6) a generalized infection of newborn calves. In the assay used for our studies, a 527 base pair product was amplified using a 51 cycle PCR process.

By using the amplification apparatus according to the invention, PCR processes can be performed using reduced volumes of initial DNA starting material and/or reduced concentrations in the DNA starting material. In an embodiment, DNA samples can be replicated with starting DNA concentrations of 1 picogram per microliter or less, or 500 femtograms per microliter or less, or 100 femtograms per microliter or less, or 50 femtograms per microliter or less, or 10 femtograms per microliter or less. In another embodiment, the initial sample volume used for amplification can be 10 microliters or less, or 5 microliters or less, or 1 microliter or less.

Figure 12:
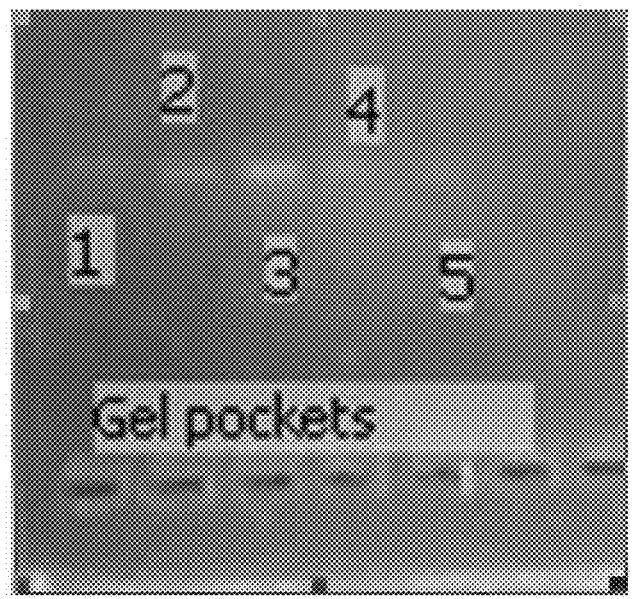
FIG. 12 depicts data collected related to a device according to an embodiment of the invention.

In an exemplary embodiment, a test chip according to an embodiment of the invention was used for amplification of IBP viral DNA. A 5 μl volume was amplified both in a conventional machine and on a chip according to the invention, respectively. FIG. 12 shows the gel image of the results. The well marked as 1 was used for the DNA ladder, well 2 was used to load the sample amplified in the conventional system and well 3 was for the sample extracted from the chamber. The post electrophoresed gel image shows bands in front of all the wells. The bands on the track 4 and 5, corresponding to the sample loaded in well 4 and 5, show amplification in the fluid extracted from the inlet and outlet ports. This demonstrates the minimal sample loss due to evaporation as well as the temperature uniformity of the whole surface being within +1° C. (PCR limit) because of better thermal conductivity of silicon.

Figure 13A:
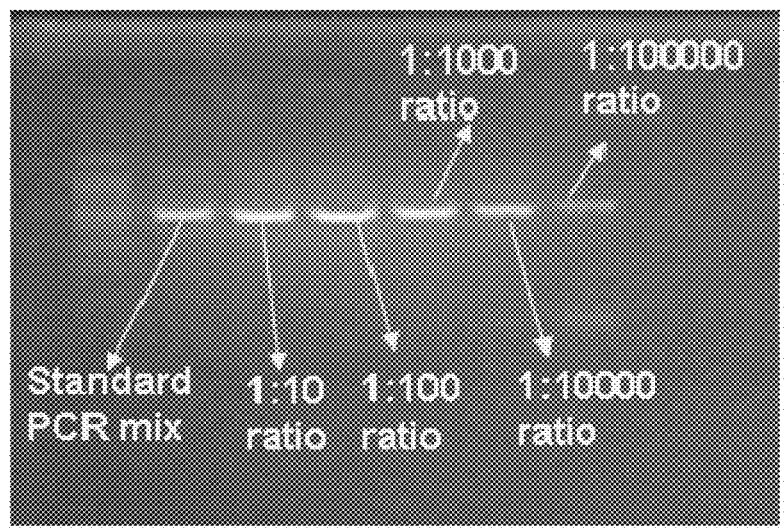
FIGS. 13A-13B depict data collected related to a device according to an embodiment of the invention.
Figure 13B:
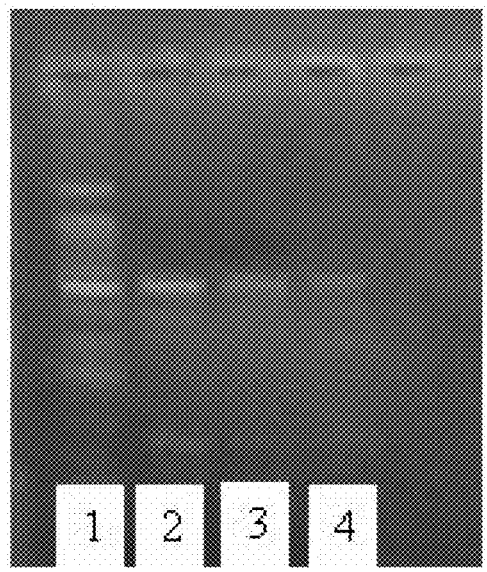

In another exemplary embodiment, the sensitivity of the amplification chamber was investigated by diluting the DNA sample with RNase-free water. Results were obtained with both a conventional thermal cycler and an on chip amplifier according to an embodiment of the invention. A standard DNA sample (conc.=50 ng/μl) was used in a conventional setup, but diluted with RNase water in the ratios 10:1, 100:1, 1000:1, 10000:1 and 100000:1.5 microliter volumes of each of these dilutions were amplified using a conventional thermo-cycler. FIG. 13A shows a slab gel image of one such trial. As shown in this image, at the 100000:1 dilution level, the band is faint. This ratio of the initial template was also tested in a micro-chamber according to the invention. Running through a slab gel generated a positive result for this dilution level, as shown in the post-electrophoresis gel image in FIG. 13B. Well No. 1 was used to load the DNA ladder, No. 2 used for sample from the conventional setup, No. 3 for the on chip chamber sample and No. 4 for the sample from one of the ports. The image shows bands in all the tracks, demonstrating that the chip developed can amplify at highly diluted concentrations of the initial template.

Figure 14A:
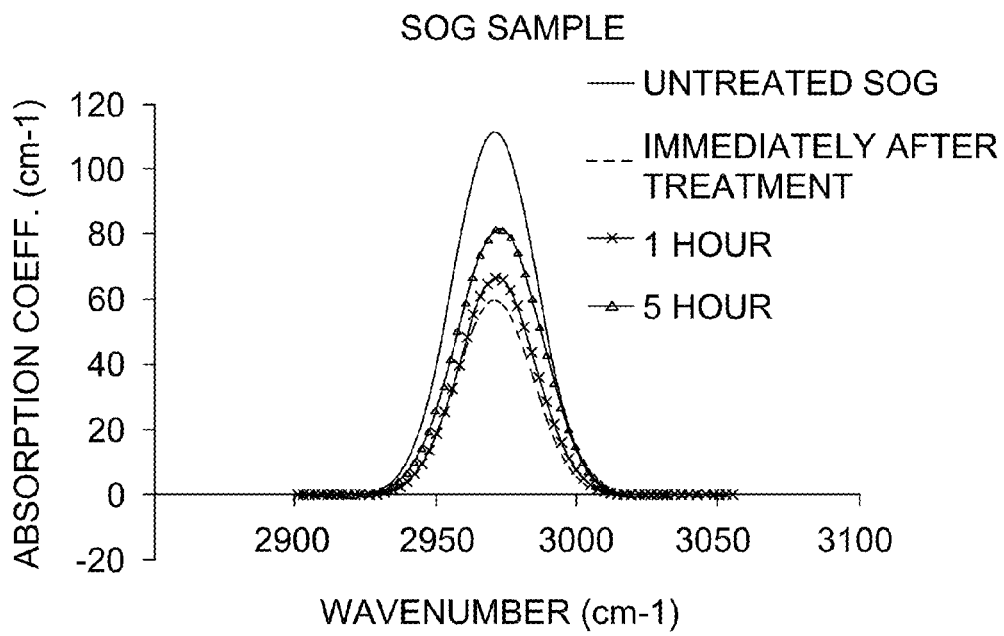
FIGS. 14A-14C depict data collected related to a device according to an embodiment of the invention.
Figure 14B:
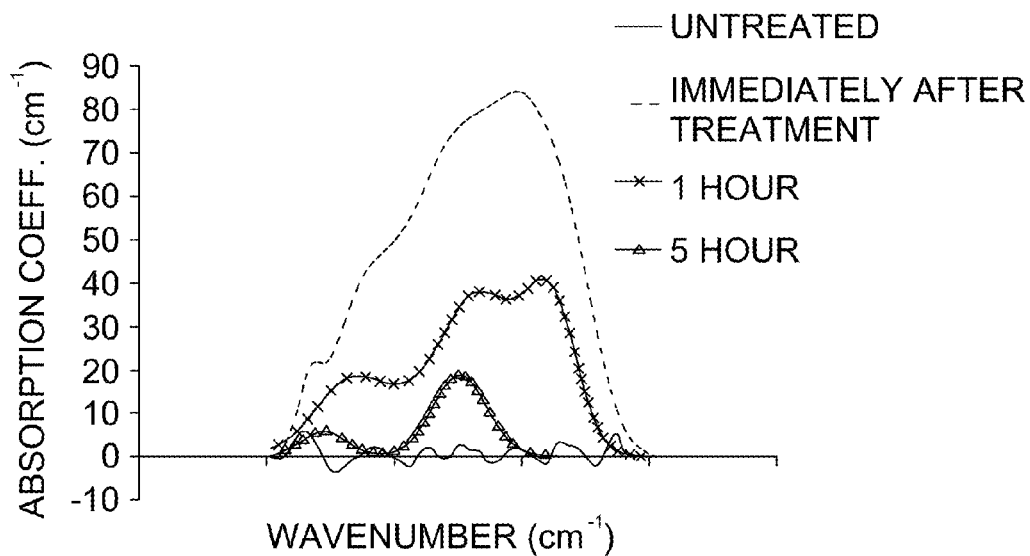
Figure 14C:
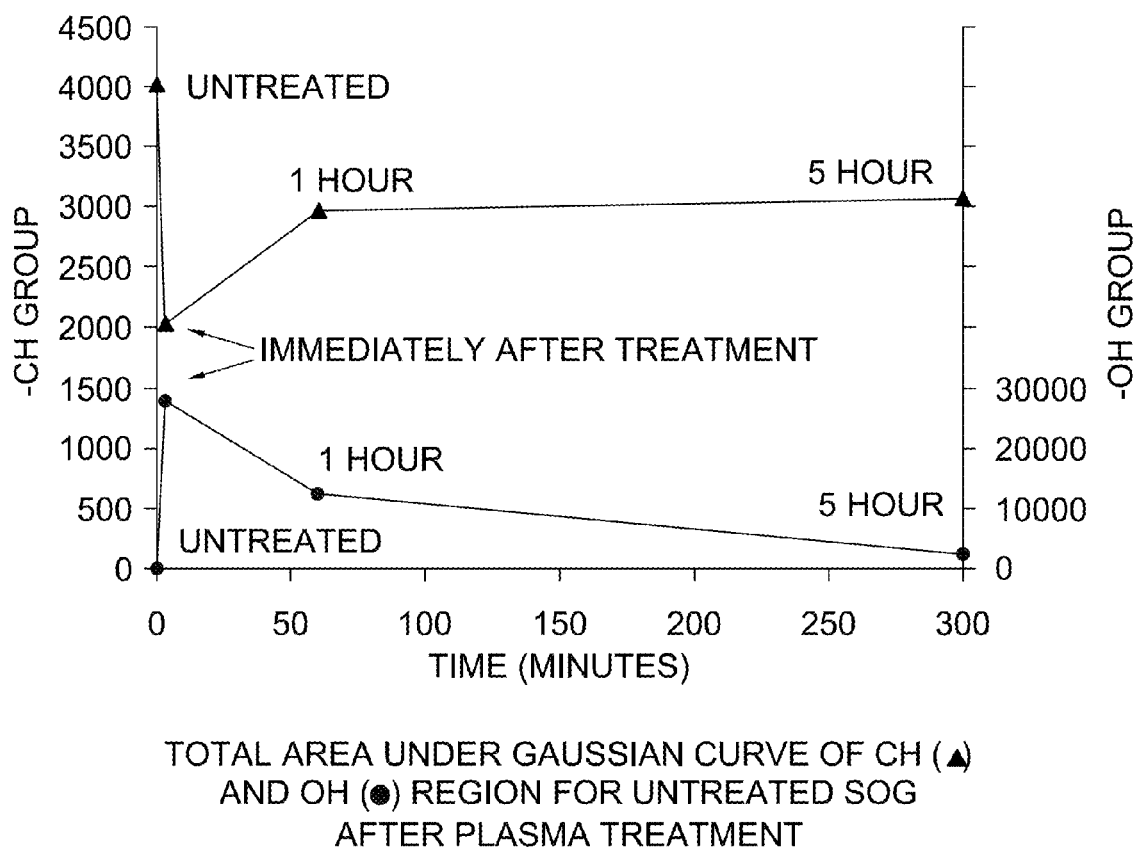

In still another embodiment, a PCR process can be repeatedly performed in an amplification device according to an embodiment of the invention. The ability to perform repeated amplification of the PCR mix is enabled in part by the fact that, unlike silicon or glass substrates, SOG is not a PCR inhibitor. One potential cause of inhibition is the ability of the DNA to preferentially bind to some substrates. This is believed to be primarily due to DNA being a charged species, which means that the DNA should not bind to non polar species. Both PDMS and SOG show post exposure surface relaxation as discussed earlier. They exhibit a gradual methylation and dehydroxylation of the surface at increasing post exposure times making the surfaces more and more non polar. FIGS. 14A and 14B show an ATR-FTIR plot of the behavior of the methylation and hydroxylation on the surface during the post-exposure relaxation of the surfaces. FIG. 14C, which shows a plot of the time varying area under the methyl and hydroxyl peak, provides a quantitative basis for determining the surface content over time. It is believed that the SOG and PDMS forming the inner walls of the chamber and ports provide a completely inert surface where there is no DNA binding, allowing for repetitive amplification in an amplification device according to the invention. Additionally, the lack of binding of DNA to the interior surfaces of an amplification device according to the invention allows the device to be used again after a successful amplification. Because the DNA does not bind to the surfaces in the amplification device, the device can be effectively cleaned to allow a second amplification process to be performed without contamination from a first amplification process. The various embodiments of the method as described provide a generalized approach to investigate the dynamics of a methyl rich polymer surface after exposure to oxygen ion bombardment. The method can be used to predict the behavior of other methyl rich polymer films that may identically form a PCR non-inhibiting surface.

VI. Bond Strength of SOG

The bond strengths of PDMS Silicon dioxide with and without an intermediate SOG coating have also been investigated. The blister separation from these substrates occurred at only 10 psi in case of Silicon dioxide without SOG intermediate layer and 75 85 psi for with the SOG layer. The SOG thus provides a much stronger seal with PDMS. Also it can realize thin continuous films over different substrates.

Figure 10:
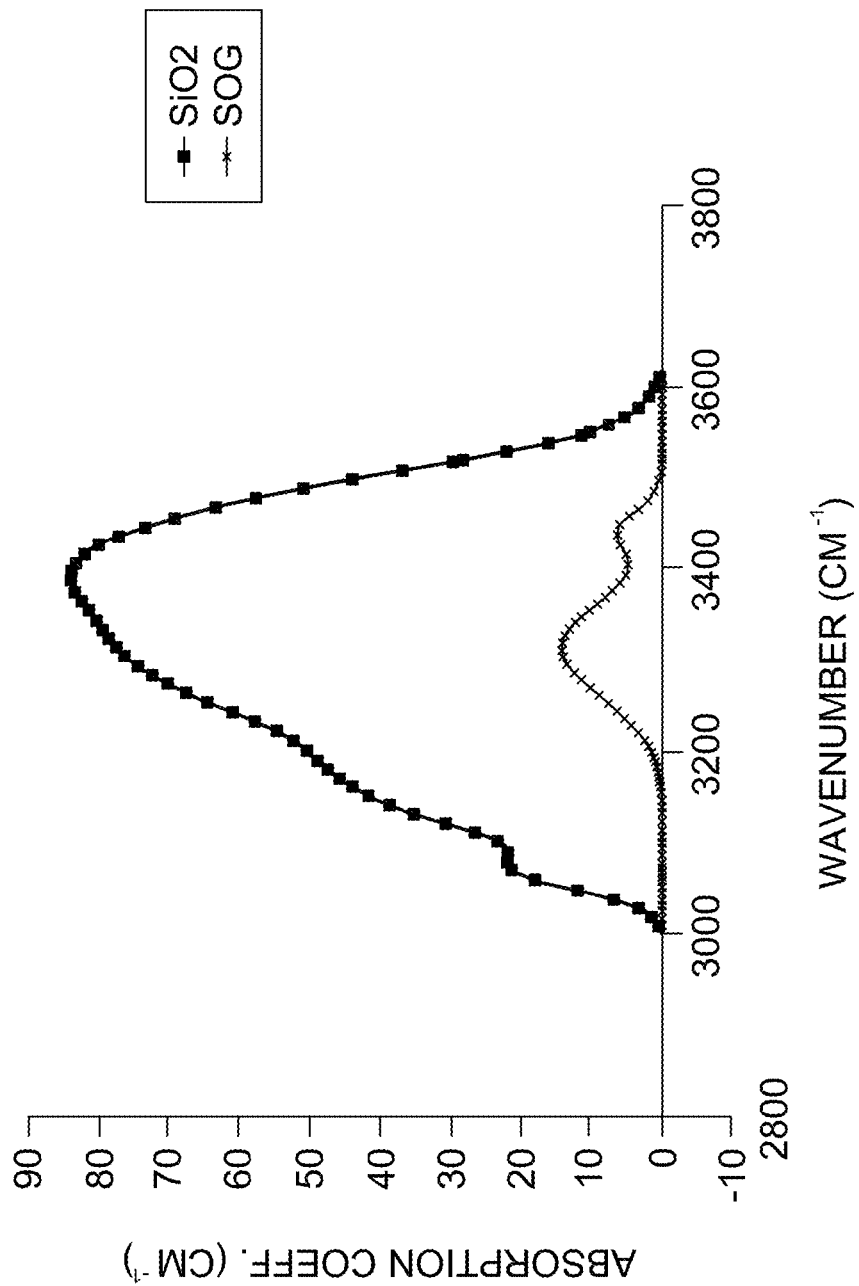
FIG. 10 is a graphical representation of the caparison between SOG and $SiO_2$ after plasma exposure in accordance with an embodiment of the present invention.

ATR FTIR spectra on the plasma exposed silicon dioxide and the SOG coated surfaces were performed using a Nicolet 4700 spectrometer. FIG. 10 shows OH stretching broad band spectra in the 3000 3600 cm-1 region for plasma treated silicon dioxide and the SOG surfaces. The strong broad absorption band that appears to be approximately at 3450 cm−1 [FIG. 10] is attributed to hydroxyl groups. The plasma treated SOG layer exhibits a much higher presence of hydroxyl groups than the plasma treated silicon dioxide, which validates our reasoning and explanation of bond strength, contact angle data. The area under the OH peak for the treated SOG sample is calculated to be 22,754 AU (Arbitrary Units) and for the treated silicon dioxide sample, it is calculated to be 2045 AU. There is approximately an order of magnitude increase in the surface OH groups on the treated SOG surface which is very close to the difference in bond strengths between the treated SOG and the silicon dioxide surface (factor of 8).

VII. Change of Contact Angle of SOG Surface with Time.

The post exposed SOG surface showed an increase in the advancing contact angle with time. Measurements were taken after 5 min., 1 hour, 5 hours and 2 days. The contact angle rose from 7 deg. immediately after exposure to around 63 deg. after 5 hours. No change in the contact angle was observed after 2 days indicating a full recovery of the surface and saturation in surface recovery rate after 5 hours [FIG. 15].

A similar surface recovery was found to occur in PDMS, earlier, due to a tendency of the methyl groups within the bulk to appear on the surface by chain scission and surface crack formation.

The SOG surface being structurally identical to PDMS should have a similar chain scission based mechanism. In order to confirm this hypothesis, an ATR FTIR spectra has again been performed on the SOG surface and a gradual methylation and dehydroxylation with post exposure relaxation time has been observed.

VIII. Non Specific Binding of DNA to Channel and Chamber Walls—Fluorescence Studies with Labeled DNA The effect of non specific binding on the hydrophobic interiors of the chamber was investigated by flowing FAM labeled RT PCR products [excitation maximum=494 nm and emission maximum=520 nm].

Figure 16:
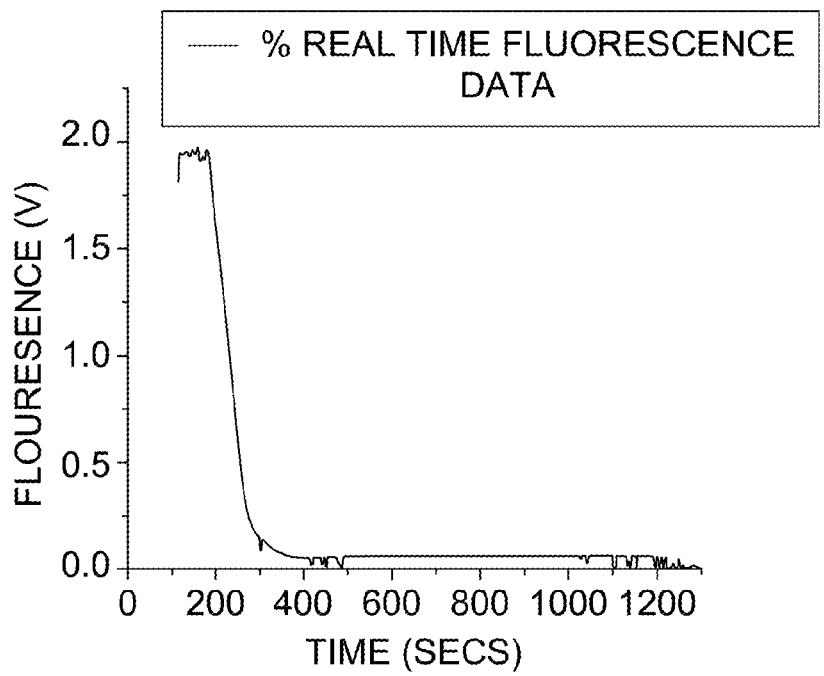
FIG. 16 depicts a graphical representation of the reduction in fluorescence intensity with time according to an embodiment of the present invention.

Two PCR devices were fabricated using a 170 micron thick SOG coated glass slide [M/Gold Seal] as the base instead of the heater patterned silicon wafer [to accommodate imaging modalities of characterization instrument]. A 1×50 Olympus inverted fluorescence microscope was used with an emission and excitation monochromator for characterization of the fluorescence intensity in the device. Ten microliter of FAM labeled RT PCR products was flown into the microchamber in one of the devices at a rate of 87 microliter/min. using a syringe pump. The fluorescence level was measured using a photodiode connected to the objective through a monochromator. The data of this photodiode is digitally acquired and plotted with time by a computer. Following this, an elution buffer solution (M/S Qiagen Inc.) was used to wash off the labeled DNA from the chip in a similar manner as described earlier for 20 min. The corresponding real time change in fluorescence intensity was plotted with time. FIG. 16 shows plots of the fluorescence intensity change observed in the device during the washcycle.

Figure 17:
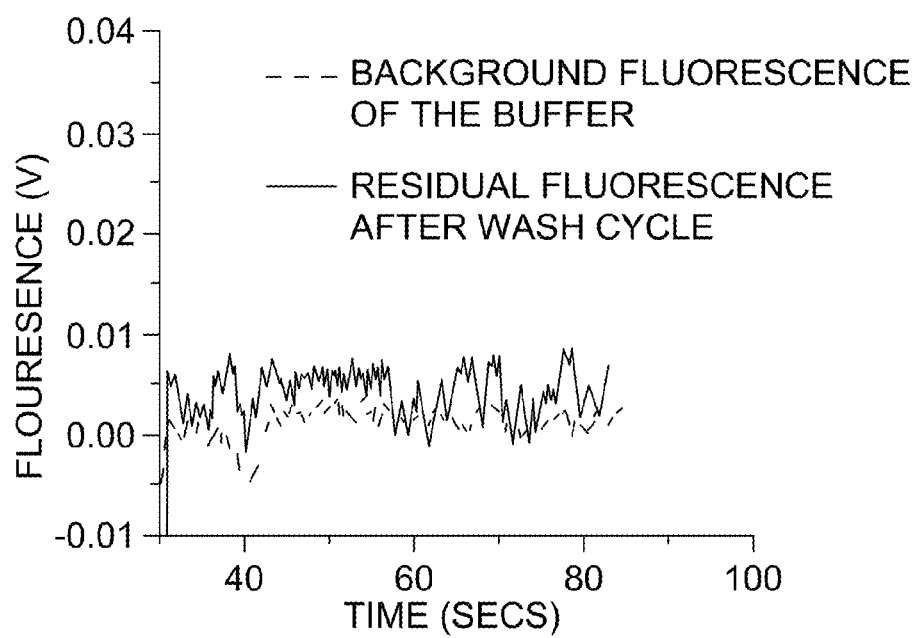
FIG. 17 depicts a graphical representation of the background fluorescence of the buffer solution and residual fluorescence left over in the microchamber in accordance with an embodiment of the present invention.

The intensity changed from 2 V to a constant 0.06 V value after 400 seconds. At the end of 1200 seconds, a forced injection of RNase free water was provided by utilizing an on chip plumbing arrangement and then the buffer flow was continued. The residual fluorescence dropped to 0.02 V after the RNase water flow and changed no further. The second device in which the labeled DNA had not been flown was injected with the washing fluids in a similar manner for background measurement purposes. FIG. 17 shows a magnified view of the background fluorescence of the buffer from the second device with the residual fluorescence left over after the wash cycle from the first device. Both parameters are plotted on the same time scale for an easy comparison. Both values superpose on each other showing that there is no non specific binding of the labeled DNA inside the chamber or channel.

IX. Heater and Resistance Temperature Detector (RTD) on the Back Side, Chamber on the Front Side.

Figure 18:
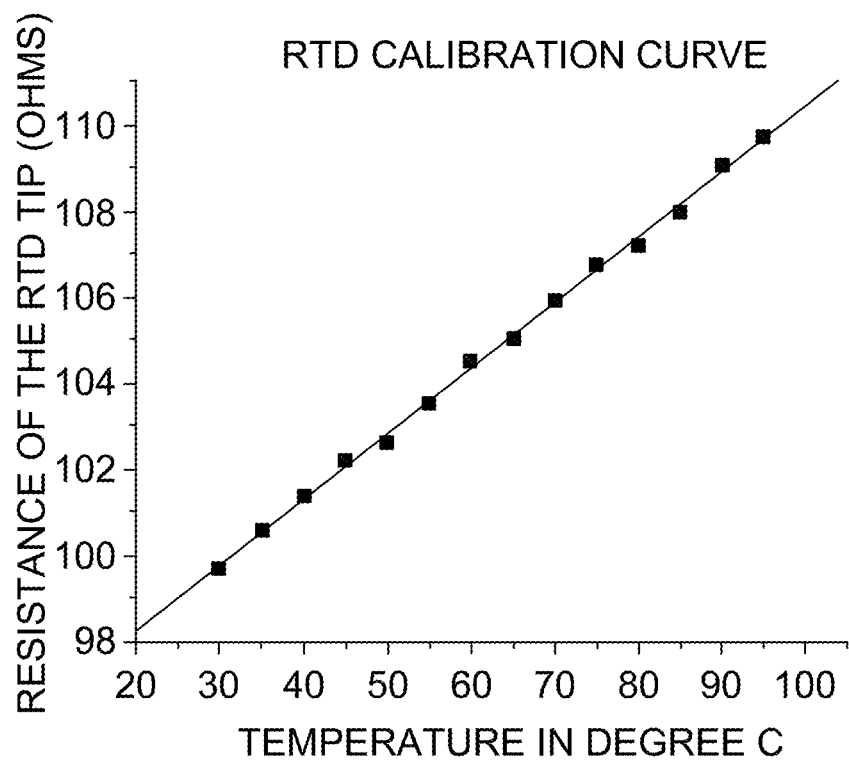
FIG. 18 depicts a graphical representation of an RTD calibration curve in accordance with an embodiment of the present invention.

The placement of the RTD plays an important role as it has a direct effect on the overall sensitivity of the device. Heaters were placed on the bottom side, RTD and chamber on the top side. This arrangement gave a good correlation between the temperature of the chamber and the resistance of the RTD. Calibrations were performed with the thermocouple placed on top surface close to the RTD. FIG. 18 shows a plot of the resistance Vs temperature.

Figure 19A:
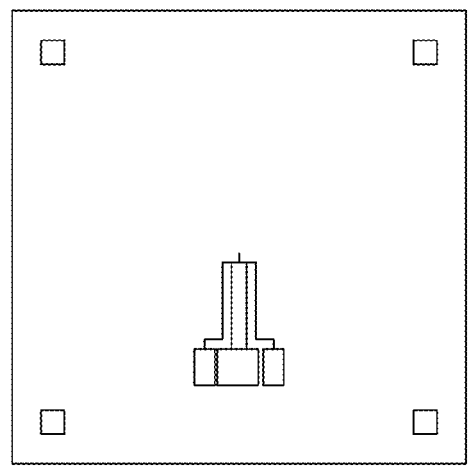
FIGS. 19A-19B depict graphical representations of a mask design for an RTD in accordance with an embodiment of the present invention.
Figure 19B:
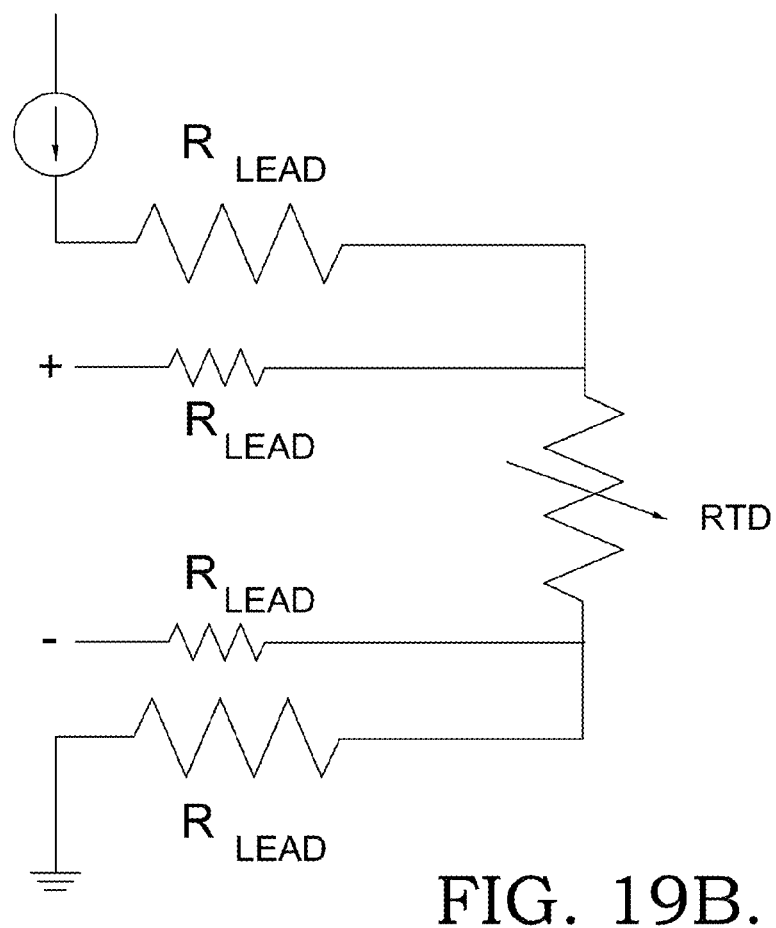

The RTD has been designed and used in the 4 wire measurement mode to minimize the measurement errors due to lead resistances. FIGS. 19A and 19B show the mask design and the temperature sensing in the 4 wire measurement mode using the RTD. A constant current of 1 mA was passed through the outer leads and the voltage measurements were made across the inner leads of the RTD.

Figure 20A:
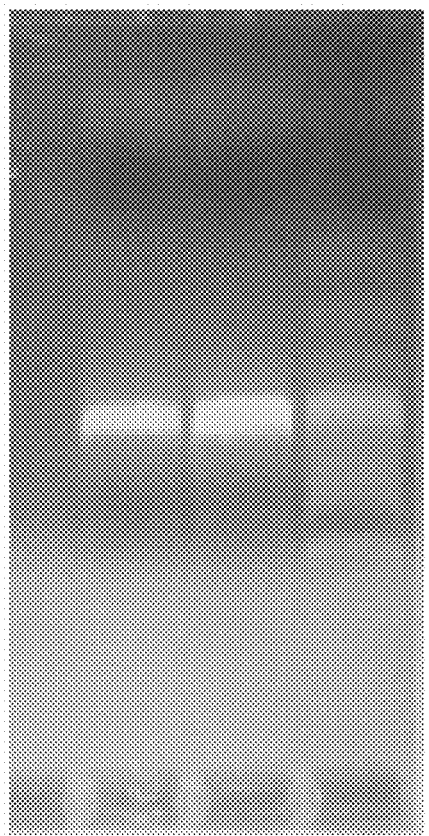
FIGS. 20A-20B depict the results of PCR applications of a 1:1 sample and a 100,000:1 sample in accordance with an embodiment of the present invention.
Figure 20B:
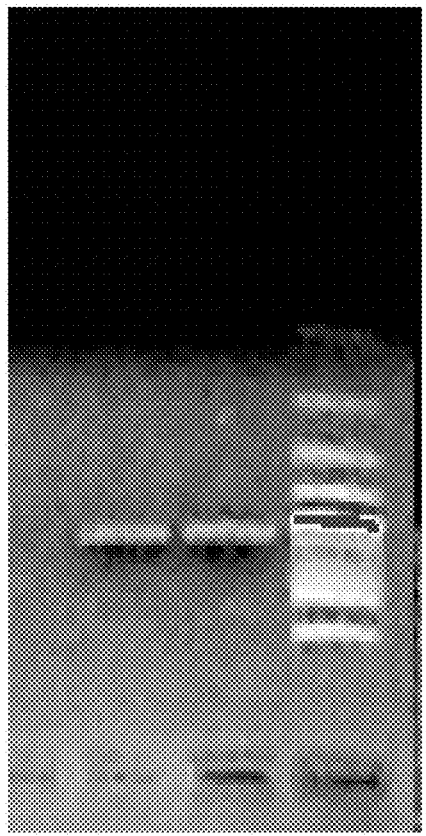

To test the fabricated device, Infectious Bovine Rhinotracheitis (IBR) virus was used as a test assay for on chip studies. The PCR amplification was performed on chip with the RTD as the temperature sensor for two different concentrations. A template DNA (7 ng/μl) and another one diluted to 100,000:1 with RNase free water were amplified on the micro-chip. Slab-gel electrophoresis was performed on the amplified samples. (FIGS. 20A-20B).

Figure 21:
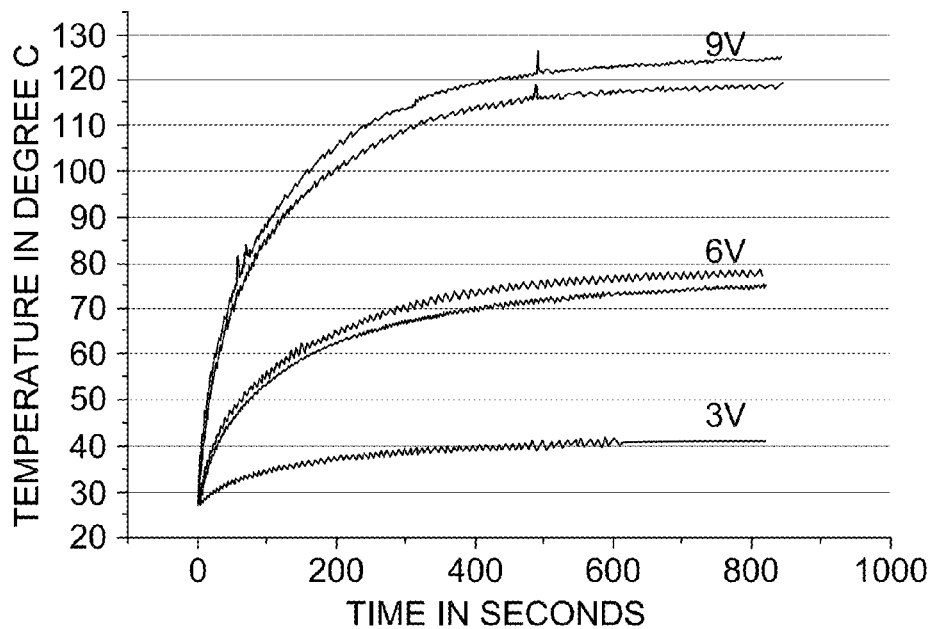
FIG. 21 depicts a graphical representation of temperature responses to different voltage steps in accordance with an embodiment of the present invention.

Parametric identification of the system was performed using ARX model assuming the system to be linear. The linearity of the system was investigated by providing three different linearly scaled voltage inputs. The corresponding temperature of the system was recorded. The steady state temperature was observed to be scaled up by the same amount as the voltage steps hence confirming the linearity. FIG. 21 gives the plot of the step temperature responses on the heater side and the chamber side of the device. On-chip RTDs fabricated on both top and bottom surfaces were calibrated and used as temperature sensors. A LabVIEW (National Instruments) code was used to apply the voltage as well as acquire the temperature data.

Figure 22:
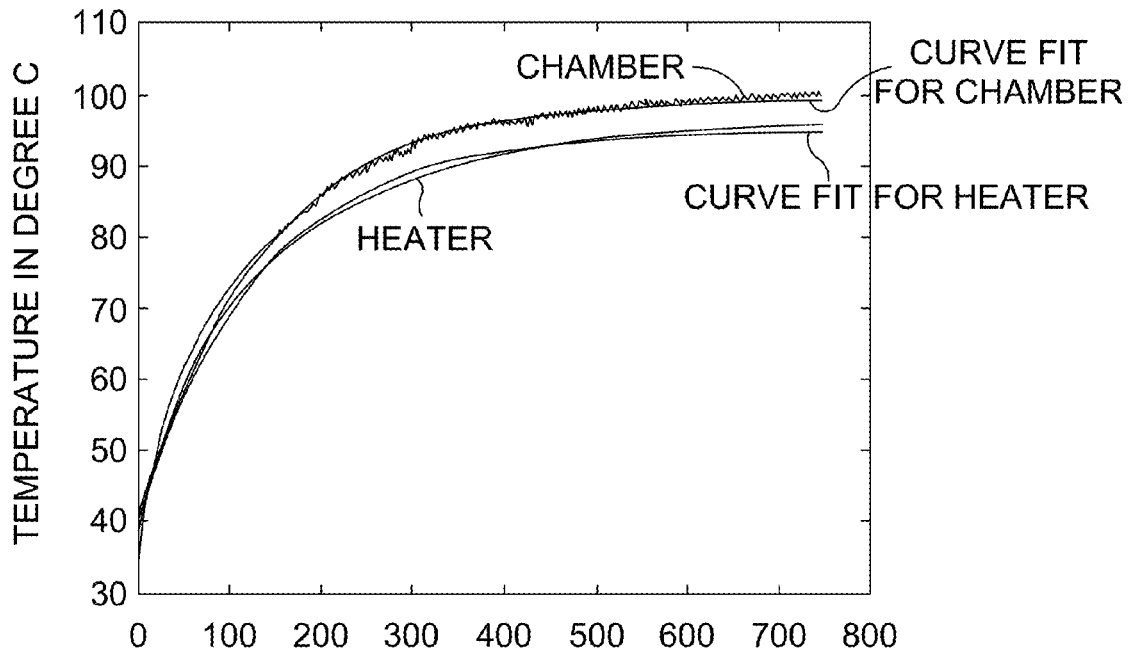
FIG. 22 depicts a graphical representation of a step response with an input voltage step of 7.5 V for the heater and chamber temperature in accordance with an embodiment of the present invention.

Extraction of model parameters using the black-box technique requires the excitation of the system with a perturbation signal and recording the output values. The perturbation signal should ideally have an autocorrelation function similar to white noise. A pseudo-random-binary sequence (PRBS) was chosen as the perturbation signal. The bit width for the PRBS signal was calculated from the estimated 3 dB bandwidth of the system. A voltage step of 7.5V was given to the system and the temperature response was recorded. An exponential curve was fitted to this response and the major time constants of the system were obtained. FIG. 22 gives the step response to a 7.5 V step and a curve fit. The bit width was calculated as $$\tau_{bitwidth} = \frac{2\pi}{3B} \quad (1)$$

$$B = \frac{1}{\tau} \quad (2)$$

where 'B' is the 3 dB bandwidth of the system estimated from the temperature step response and 'τ' is the time constant. The following exponential equation was used to fit the data for the obtained step responses on the top and bottom surfaces. Table 2, below, displays the curve fit parameters for the responses.

$$T = T_{max}(1 - e^{-(t+t_o)/\tau}) \quad (3)$$

TABLE 2

| | $T_{max}$ | $t_o$ (Seconds) | τ |
|---|---|---|---|
| Heater Side | 99.28 | 132 | 69.57 |
| Chamber Side | 95.17 | 136 | 74.81 |

Figure 23:
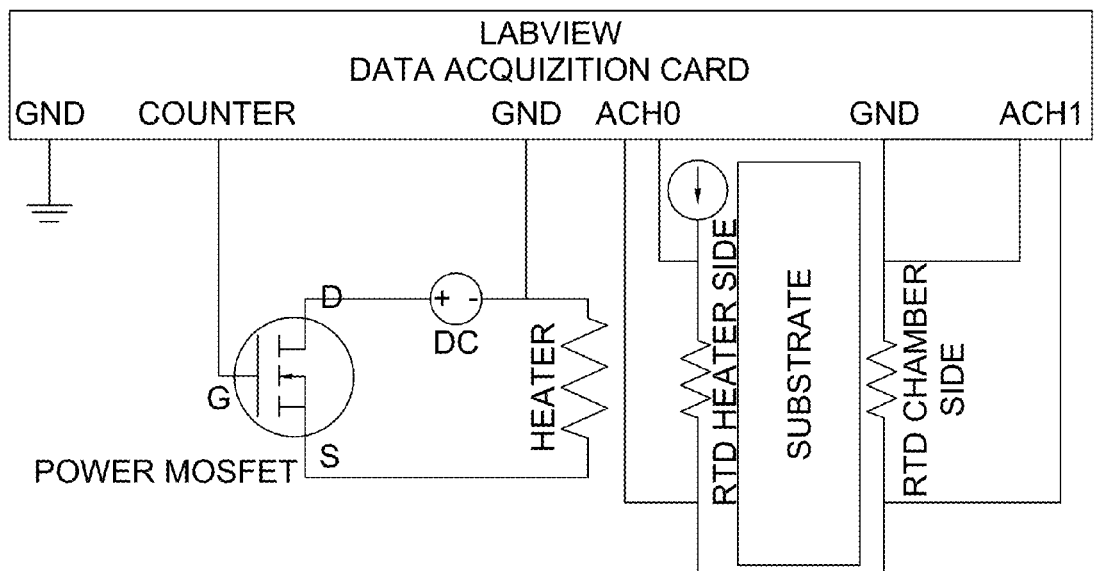
FIG. 23 depicts a diagram of a circuit in accordance with an embodiment of the present invention.
Figure 24:
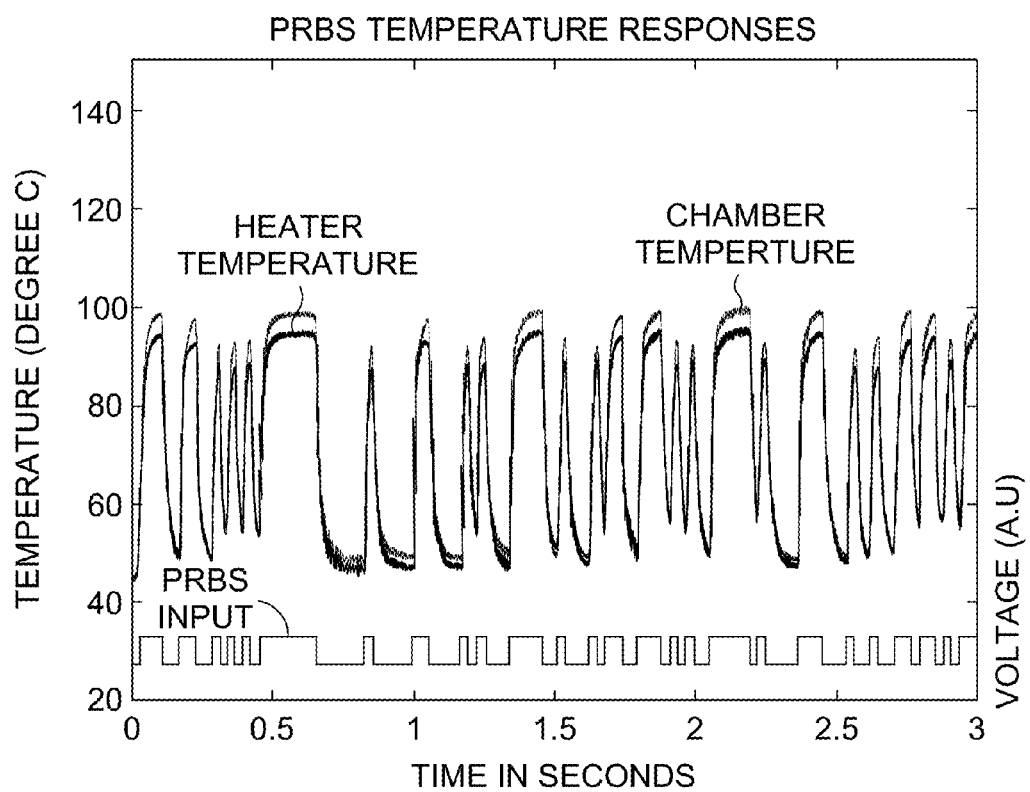
FIG. 24 depicts a diagram of a PRBS temperature response of the heater side and the chamber side in accordance with an embodiment of the present invention.

A $7^{th}$ order modulo-2 primitive polynomial was chosen for the generation of the PRBS signal. The output from the LabVIEW DAQ card was used to control the turn on/off times of the supply to the heater. The representative circuit diagram for the experimental set-up is shown in FIG. 23. A 7.5 V D.C supply was used and the duty cycle of the counter was switched between 1 and 0.25 corresponding to voltage values of 7.5V and 1.85 V. A duty cycle of 0.25 and 1 corresponded to a steady state chamber temperature of 60 C and 96 C respectively. Thus, the temperature of the chamber was switched between 96 and 60 C [temperature range of interest for any standard PCR cycle]. FIG. 24 gives the PRBS responses of the system.

The D.C component from the output response and the PRBS voltage input was removed by subtracting both these signals from their corresponding mean values prior to performing the parametric fits. Different order ARX models have been identified based on the PRBS input-output data. We observed a decrease in the mean squared error between the simulated and the experimental responses as the model order was increased.

Figure 25:
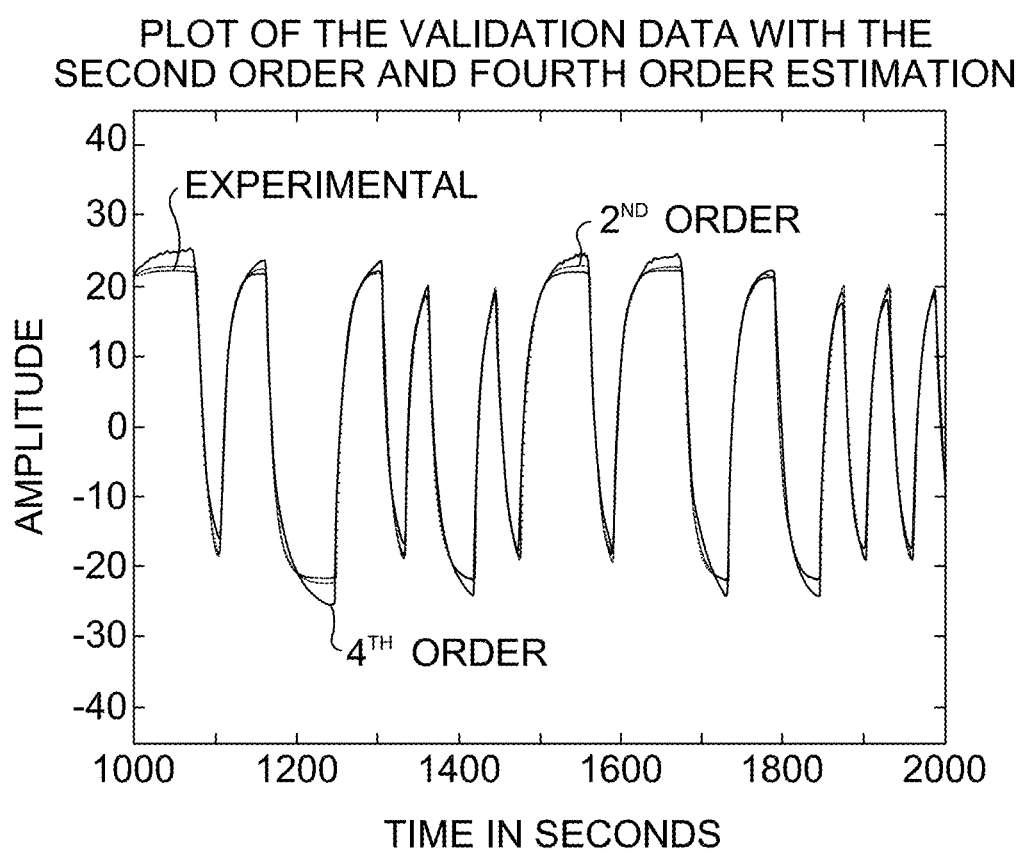
FIG. 25 depicts a graphical representation plot of the simulated response with second order model and fourth order model in accordance with an embodiment of the present invention.

FIG. 25 gives the simulated data with a second order and a fourth order models for the chamber temperature. The mean squared error (MSE) for the second order model was calculated to be 7.2691, while the MSE for the fourth order model was obtained to be 5.2924. The second order ARX model obtained can be presented by $$A(q^{-1})ych(k)=B(q^{-1})U(k)\quad(\ )$$

where
$A(q^{-1})=1-0.8163\ q^{-1}-0.07538q^{-2}$
$B(q^{-1})=0.8475\ q^{-1}$

Figure 26:
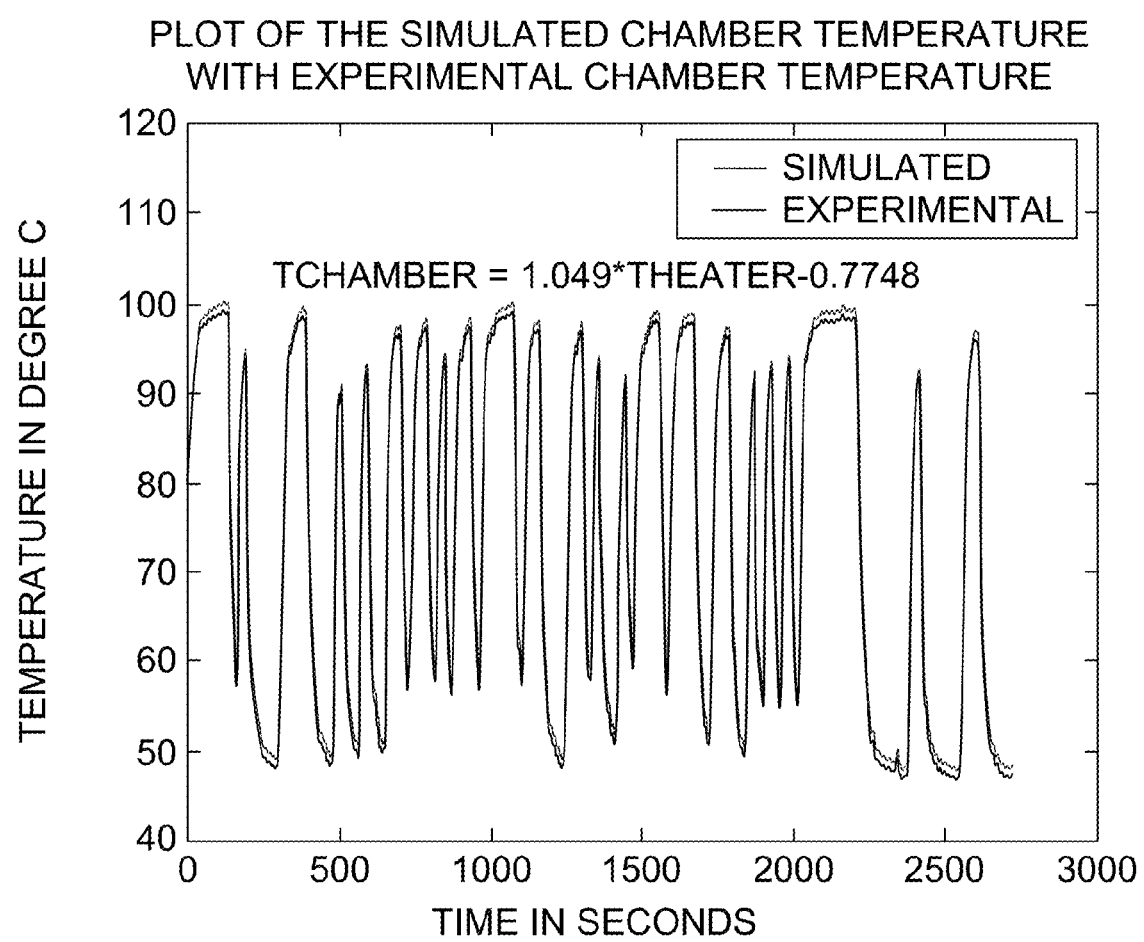
FIG. 26 depicts a graphical representation of a simulated chamber temperature response in accordance with an embodiment of the present invention.

The obtained parameters for both the fourth order model were
$A(q^{-1})=1-0.7508\ q^{-1}+0.00199^{-2}+0.06221\ q^{-3}-0.1781\ q^{-4}$
$B(q-1)=1-0.87\ q^{-1}$ In addition to the identification of the system parameters, a relation was derived between the chamber temperature and the heater temperature. This would facilitate the placement of the RTD on the bottom surface (heater side), thus significantly simplifying the fabrication process for the PCR microchip. The obtained PRBS responses for the bottom and the top surface temperatures were used and different models were assumed to fit the input-output relations using the least squares method. It has been observed that the relation between the heater temperature and the chamber temperature could be expressed as a simple first order linear equation accurately. This equation has been used to simulate the chamber temperature and compare with experimental chamber temperature. FIG. 26 shows the simulated and the actual values.

X. Alternate Uses

While the PDMS device is presently shown for use with a PCR amplification device, it will be appreciated that a PDMS structure bonded to an SOG coated silicon substrate may be utilized in other microfluidic applications, including, but not limited to, genomics, proteomics, metabolomics, micronscale heat transfer processes such as in computer chips or outdoor electrical power applications.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

What is claimed is:

1. A method for amplifying a DNA sample on an amplification chip for DNA amplification, the method comprising:
   providing the DNA sample having a concentration of 1 picogram per microliter or less;
   denaturing the DNA sample on the amplification chip, wherein the inner surfaces of the amplification chip consist of a polydimethylsiloxane layer bonded to a spin-on glass layer;
   associating the DNA sample with primers on the amplification chip; and
   amplifying the DNA sample on the amplification chip.

2. The method of claim 1, wherein the provided DNA sample has a concentration of 100 femtograms per microliter or less.

3. The method of claim 1, further comprising: introducing the DNA sample in a chamber of the amplification chip.

4. The method of claim 3, wherein the chamber of the amplification chip is located between the polydimethylsiloxane layer and the spin-on glass layer.

5. The method of claim 1, wherein the spin-on glass comprises methyl silsequioxane.

* * * * *